US009269168B2

(12) United States Patent
Inglese et al.

(10) Patent No.: US 9,269,168 B2
(45) Date of Patent: Feb. 23, 2016

(54) VOLUME IMAGE RECONSTRUCTION USING DATA FROM MULTIPLE ENERGY SPECTRA

(71) Applicant: Carestream Health, Inc., Rochester, NY (US)

(72) Inventors: Jean-Marc Inglese, Bussy Saint Georges (FR); Jay S. Schildkraut, Rochester, NY (US)

(73) Assignee: Carestream Health, Inc., Rochester, NY (US)

(*) Notice: Subject to any disclaimer, the term of this patent is extended or adjusted under 35 U.S.C. 154(b) by 53 days.

(21) Appl. No.: 13/834,758

(22) Filed: Mar. 15, 2013

(65) Prior Publication Data
US 2014/0270440 A1 Sep. 18, 2014

(51) Int. Cl.
*G06T 11/00* (2006.01)
*A61B 6/00* (2006.01)
*A61B 6/14* (2006.01)
*A61B 6/03* (2006.01)

(52) U.S. Cl.
CPC .............. *G06T 11/006* (2013.01); *A61B 6/4241* (2013.01); *A61B 6/482* (2013.01); *A61B 6/501* (2013.01); *A61B 6/5205* (2013.01); *A61B 6/032* (2013.01); *A61B 6/14* (2013.01); *A61B 6/4085* (2013.01); *A61B 6/4441* (2013.01); *A61B 6/5258* (2013.01); *G06T 2211/408* (2013.01); *G06T 2211/424* (2013.01)

(58) Field of Classification Search
None
See application file for complete search history.

(56) References Cited

U.S. PATENT DOCUMENTS

| 5,677,940 | A | 10/1997 | Suzuki et al. | |
|---|---|---|---|---|
| 6,118,842 | A | 9/2000 | Arai et al. | |
| 2009/0086884 | A1* | 4/2009 | Krauss | 378/5 |
| 2009/0122953 | A1* | 5/2009 | Imai | 378/5 |
| 2009/0207967 | A1* | 8/2009 | Liu et al. | 378/5 |
| 2009/0304249 | A1* | 12/2009 | Wu | 382/131 |
| 2013/0053689 | A1* | 2/2013 | Das et al. | 600/425 |

FOREIGN PATENT DOCUMENTS

DE  10 2009 015 772  8/2010

OTHER PUBLICATIONS

MaaB, Exact dual energy material decomposition from inconsistent rays (MDIR), published in 2011.*

(Continued)

*Primary Examiner* — Vu Le
*Assistant Examiner* — Alexander J Lesnick

(57) ABSTRACT

A method for forming a three-dimensional reconstructed image acquires two dimensional measured radiographic projection images over a set of projection angles, wherein the measured projection image data is obtained from an energy resolving detector that distinguishes first and second energy bands. A volume reconstruction has image voxel values representative of the scanned object by back projection of the measured projection data. Volume reconstruction values are iteratively modified to generate an iterative reconstruction by repeating, for angles in the set of projection angles and for each of a plurality of pixels of the detector: generating a forward projection that includes calculating an x-ray spectral distribution at each volume voxel, calculating an error value by comparing the generated forward projection value with the corresponding measured projection image value, and adjusting one or more voxel values using the calculated error value and the x-ray spectral distribution. The generated iterative reconstruction displays.

15 Claims, 22 Drawing Sheets

(56) References Cited

OTHER PUBLICATIONS

LaCroix et al. "Investigation of the Use of X-ray CT Images for Attenuation Compensation in SPECT," published in 1994.*

Schmidt, "Optimal "image-based" weighting for energy-resolved CT," published in 2009.*

Elbakri, "Statistical Reconstruction Algorithms for Polyenergetic X-ray Computed Tomography," with relevant portions highlighted.*

Clemens Maaβ et al., "Exact Dual Energy Material Decomposition From Inconsistent Rays (MDIR)", Medical Physics, vol. 38, No. 2, Feb. 2011, pp. 691-700.

Clemens Maaβ et al., "Image-Based Dual Energy CT Using Optimized Precorrection Functions: A Practical New Approach of Material Decomposition in Image Domain", Medical Physics, vol. 36, No. 8, Aug. 2009, pp. 3818-3829.

Timothy P. Szczykutowicz et al., "Dual Energy CT Using Slow kVp Switching Acquisition and Prior Image Constrained Compressed Sensing", Physics in Medicine and Biology, Institute of Physics Publishing, vol. 55, No. 21, Oct. 12, 2010, pp. 6411-6429.

Idris A. Elbakri, "Statistical Reconstruction Algorithms for Polyenergetic X-ray Computed Tomography", Dissertation, Jan. 2, 2003, pp. 1-175.

International Search Report for International Application No. PCT/US2014/022906 mailed on Aug. 8, 2014, 4 pages.

* cited by examiner

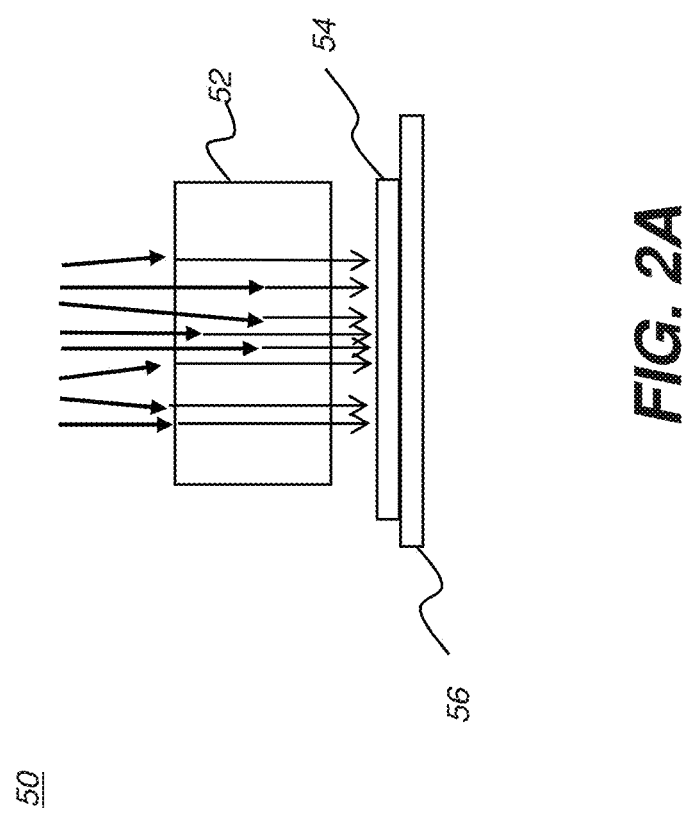

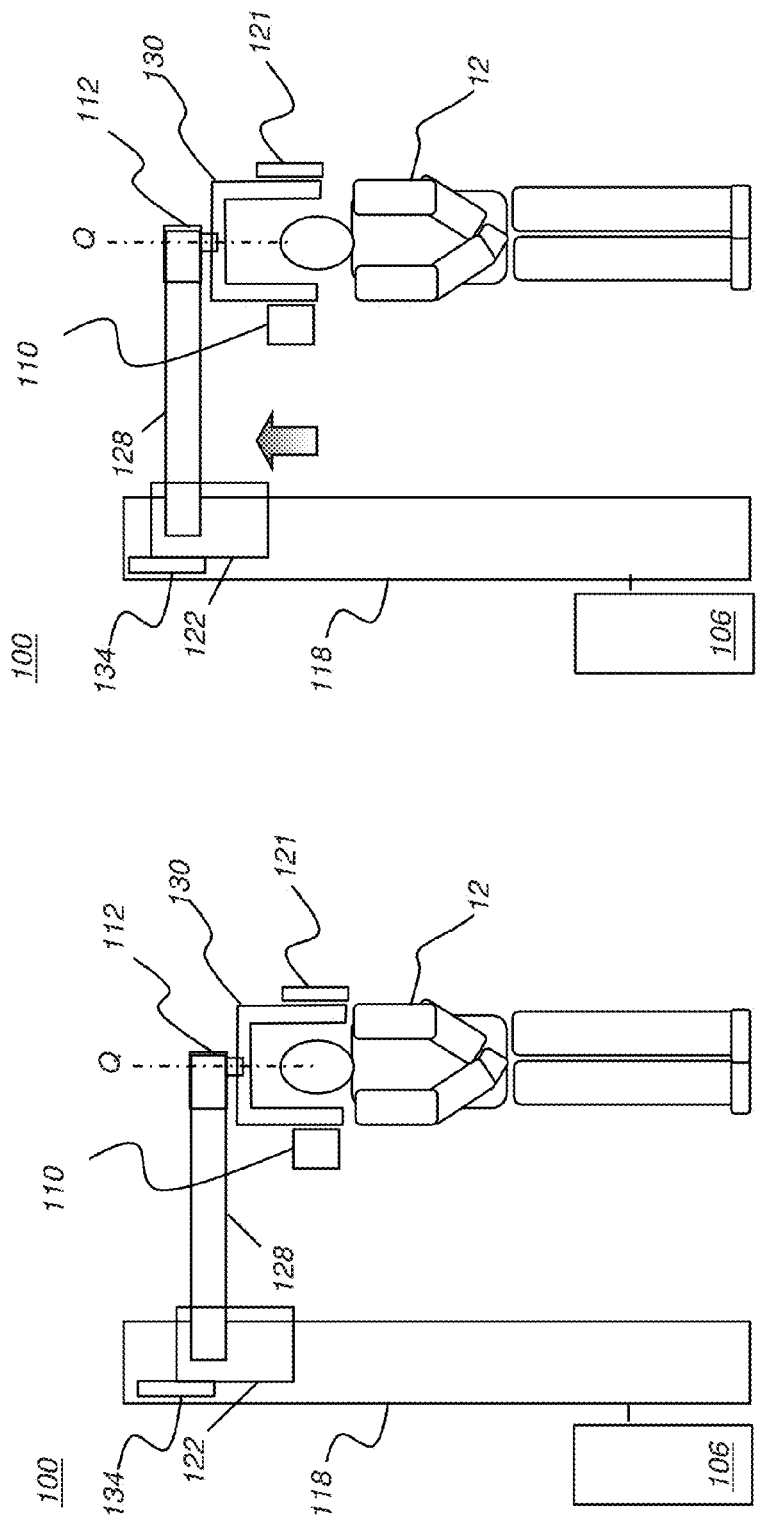

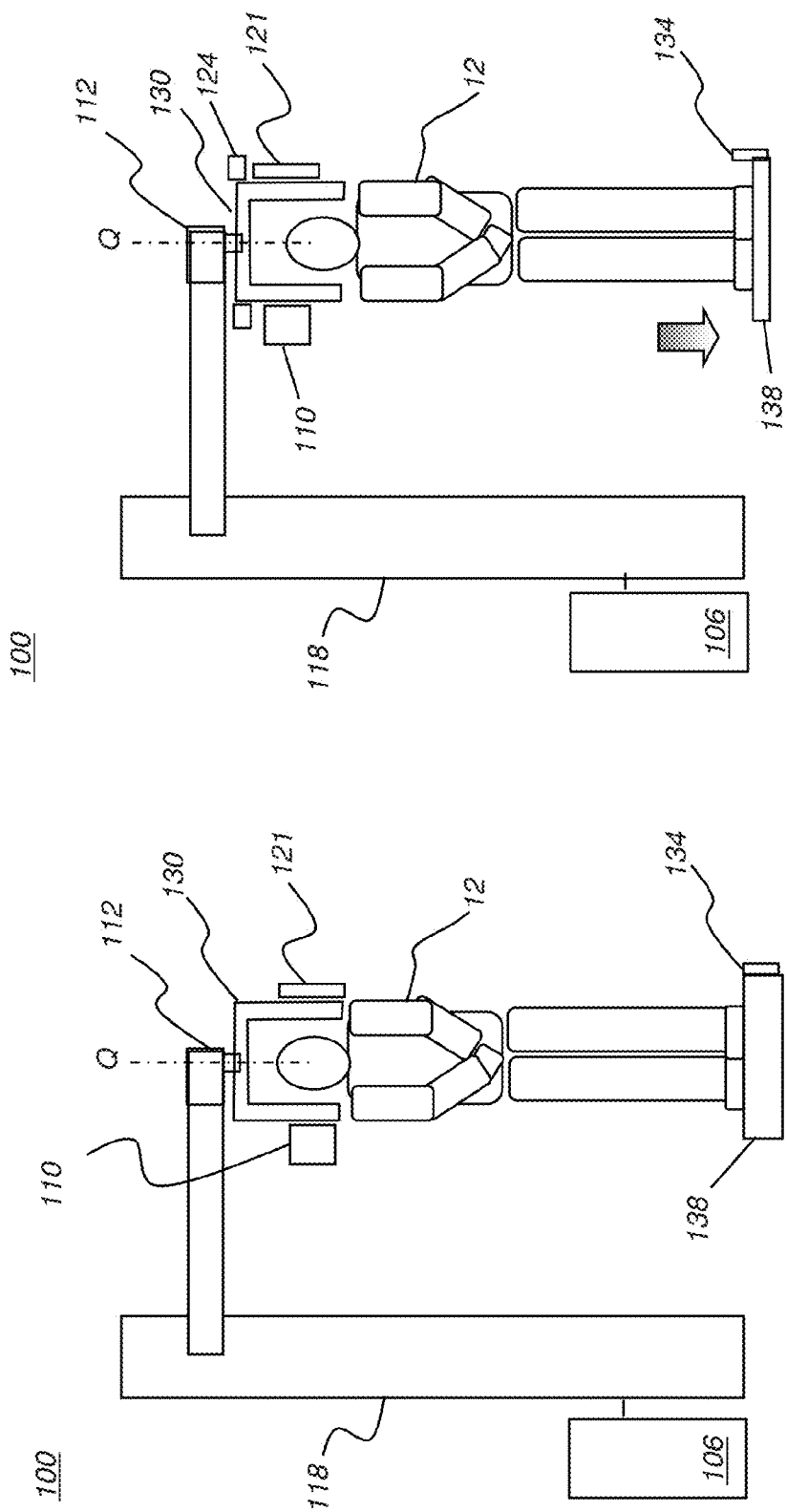

VOLUME IMAGE RECONSTRUCTION USING DATA FROM MULTIPLE ENERGY SPECTRA

FIELD OF THE INVENTION

The invention relates generally to the field of radiographic imaging and more particularly to apparatus and methods for obtaining volume images of a patient, such as images of the head.

BACKGROUND OF THE INVENTION

A computerized tomography (CT) imaging apparatus operates by acquiring multiple 2D images with a rotating imaging ensemble or gantry that has an x-ray source and, opposite the x-ray source, an imaging sensor rotating about a fixed axis relative to the patient. CT imaging allows the reconstruction of 3D or volume images of anatomical structures of the patient and is acknowledged to be of particular value for obtaining useful information for assisting diagnosis and treatment.

There is considerable interest in the use of CT imaging in dental and ear-nose-throat (ENT) applications, as well as for other imaging of the patient's head. A number of volume imaging system designs have been proposed for this purpose. Among proposed solutions are hybrid systems that combine panoramic imaging and CT imaging. For example, U.S. Pat. No. 6,118,842 entitled "X-RAY IMAGING APPARATUS" to Arai et al. discloses an X-ray imaging apparatus that supports both imaging modes. The apparatus includes an X-ray source, an X-ray detector for detecting X-rays having passed through the subject, and supporting means for supporting the X-ray source and the X-ray detector so that they are spatially opposed to each other across the subject; and mode switching means for switching between a CT mode and a panorama mode. To detect X-rays, only one large area X-ray detector is used. The X-ray imaging apparatus can obtain both types of images by switching modes during the imaging session. However, the proposed imaging apparatus requires an expensive detector capable of carrying out both imaging functions in a satisfactory manner. Additionally, systems of this type typically compromise image quality by using a uniform distance between the X-ray source and detector, even though different distances would be more advantageous.

By way of example, FIG. 1 shows an embodiment of a conventional CT imaging apparatus 40. A column 18 is adjustable for height of the subject. The patient 12 or other subject, shown in dotted outline, is positioned between an x-ray source 10 and an x-ray imaging sensor panel 20, also termed an imaging detector. X-ray imaging sensor panel 20 rotates on a rotatable mount 30 in order to position a CT sensor 21 for obtaining the exposure. CT sensor 21 is positioned behind the subject, relative to x-ray source 10. The operator rotates CT sensor 21 into this position as part of imaging setup. With rotation of mount 30, sensor 21 and source 10 revolve about the head of the patient, typically for some portion of a full revolution. Still other dental imaging system solutions combine CT, panoramic, and cephalometric imaging from a single apparatus. With such combined systems, the required amounts of radiation exposure can be a concern, particularly for CT imaging, which can require numerous images, each from a separate exposure.

Conventional digital radiography detectors have some limitations related to how attenuation of radiation energy at a single exposure is interpreted. For example, it can be very difficult, from a single exposure, to distinguish whether an imaged object has a given thickness or a given attenuation coefficient. To resolve this ambiguity, some systems provide separate, sequential low-energy and higher energy exposures and use the resulting difference in image information to distinguish between types of materials. However, in order to provide this information, this type of imaging requires that the patient be subjected to additional radiation for the second exposure. This problem can be compounded for CT imaging, in which multiple images are obtained, one from each of a number of angles of revolution about the patient.

Computed tomography (CT) and cone beam computed tomography (CBCT) systems reconstruct volume image data from a series of 2D x-ray images, termed "projection images", obtained at different angular positions about the imaged subject. An iterative reconstruction method is employed to use data from the 2D images for this purpose.

Cone beam scanners generally use polychromatic X-ray sources because of their lower cost and availability as compared with monochromatic X-ray sources which either require a synchrotron or an X-ray monochromator. The broad-spectrum radiation that is emitted from the polychromatic X-ray source is attenuated by the material that is being imaged, according to its x-ray attenuation coefficient, which varies with the type of material.

Among the problems encountered in obtaining image data for accurate 3D reconstruction is beam hardening. Beam hardening occurs as the polychromatic or polyenergetic radiation progresses through the subject material. Energy of different wavelengths is absorbed at different rates, according to the irradiated subject material. As a result of energy absorption of particular wavelengths by the material, the energy spectrum of the polychromatic X-ray radiation varies with location or depth in the scanned object and this variation depends on both the spatial characteristics or depth of the object and the relative location of the X-ray source. Because lower-energy radiation (at lower frequencies or longer wavelengths) is attenuated more strongly than higher-energy radiation (at higher frequencies or shorter wavelengths), the radiation beam is "hardened". For a uniform cylindrical phantom, for example, X rays passing through the middle portion of the phantom pass through more material than X-rays passing through edge portions. As the X-ray energy encounters more material, its spectral content changes and is considered to be more "hardened" than the same energy directed through less material; the proportion of higher energy to lower energy increases as the radiation travels further through the object. From a spectral aspect, the energy spectrum changes along the beam path that the radiation follows through the material, even where the object is of uniform depth and material composition. This change in the spectral content of the beam causes artifacts such as cupping, in which the middle of the subject experiences different radiation levels than portions of the edge of the subject. These beam hardening artifacts can appear as dark bands between highly attenuating parts of the imaged object.

Beam hardening complicates the task of 3D image reconstruction in CBCT and other volume imaging modalities. The 2D image content that is used to reconstruct a particular 3D voxel can be affected differently according to the angle at which the 2D image is obtained and the location of the voxel within the imaged object. Thus, there is a need for image processing methods that compensate for beam hardening in 2D images and in 3D image reconstruction.

In conventional CBCT volume reconstruction, the volume image that is generated provides only a single data value for each voxel, according to the total amount of attenuation measured at each position within the object. This single data value is not sufficient for determining the material composition at that voxel; only a rough guess of the material combination can be made. It would be of particular value to be able to obtain additional information for each voxel. Attenuation coefficients at two or more different energy levels, for example, would provide sufficient information to allow a more accurate estimate of the material composition of the reconstructed data.

SUMMARY OF THE INVENTION

Embodiments of the present invention address the need for advancing the imaging arts, particularly for imaging of the head. Embodiments of the present invention adapt photon-counting and related imaging solutions to the problem of imaging for dental, ENT, and related applications. Using embodiments of the present invention, a medical practitioner can obtain useful images for patient treatment, taking advantage of reduced exposure levels and other advantages that photon-counting solutions provide.

The iterative reconstruction method of the present invention can be used to reduce or eliminate beam hardening artifacts in cone beam CT reconstruction. The iterative reconstruction method of the present invention is capable of resolving the detected x-rays into two or more energy bands that help to identify the material composition of the scanned object. This can be accomplished by transforming the X-ray attenuation coefficient at points in the reconstruction from polychromatic to monochromatic values at one or more reference monochromatic energies.

For systems that resolve the detected X-rays into bands, two or more monochromatic attenuation coefficients are obtained that can be used to determine the material composition of the object. Examples of energy resolving conebeam scanners include scanners with multiple X-ray source energies, devices using multiple X-ray sources or source filtration, systems using multiple detectors with different spectral sensitivity, or systems using photon counting detectors that are able to resolve the energy of the counted photons.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for forming a three-dimensional reconstructed image of an object, the method comprising:
  a) acquiring a plurality of two dimensional measured radiographic projection images scanned over a set of projection angles about the object, wherein the measured projection image data is obtained from an energy resolving detector that distinguishes at least first and second energy bands;
  b) forming a volume reconstruction comprising image voxels having values representative of the scanned object by back projection of the measured projection image data;
  c) iteratively modifying the volume reconstruction voxel values to generate an iterative reconstruction by repeating, for each angle in the set of projection angles and for each of a plurality of pixels of the detector, the steps of: generating a forward projection that includes calculating an x-ray spectral distribution at each volume reconstruction voxel, calculating an error value by comparing the generated forward projection value with the corresponding measured projection image value from the corresponding measured projection image, and adjusting one or more voxel values in back projection using the calculated error value and the x-ray spectral distribution at the voxel;
  and
  d) displaying the generated iterative reconstruction.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 2A is a schematic view that shows a digital detector using a scintillator in conventional digital radiographic imaging.

FIGS. 9A and 9B show the imaging apparatus that provides a helical scan by changing the elevation of a support arm during revolution about the patient.

FIGS. 11A and 11B show the imaging apparatus that provides a helical scan by changing the elevation of the patient's head relative to the digital sensor and radiation source during revolution about the patient.

DETAILED DESCRIPTION

Figure 1:
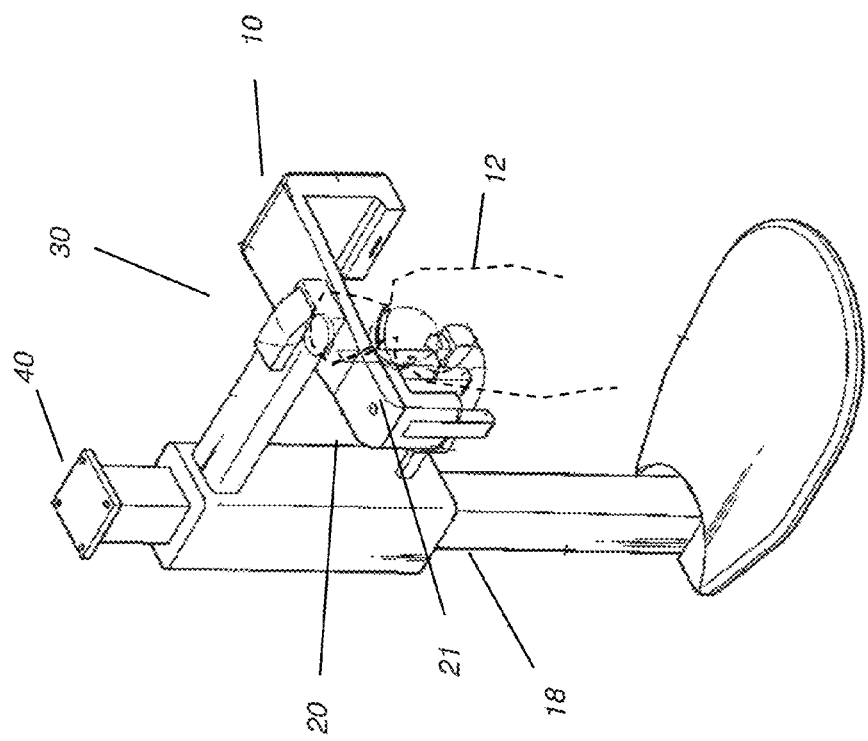
FIG. 1 shows a CT imaging apparatus for dental or ear-nose-throat (ENT) imaging.

The following is a description of exemplary embodiments of the invention, reference being made to the drawings in which the same reference numerals identify the same elements of structure in each of the several figures.

In the context of the present disclosure, the terms "pixel" and "voxel" may be used interchangeably to describe an individual digital image data element, that is, a single value representing a measured image signal intensity. Conventionally an individual digital image data element is referred to as a voxel for 3-dimensional volume images and a pixel for 2-dimensional images. Volume images, such as those from CT or CBCT apparatus, are formed by obtaining multiple 2-D images of pixels, taken at different relative angles, then combining the image data to form corresponding 3-D voxels. For the purposes of the description herein, the terms voxel and pixel can generally be considered equivalent, describing an image elemental datum that is capable of having a range of numerical values. Voxels and pixels have the attributes of both spatial location and image data code value.

In the context of the present disclosure, the term "code value" refers to the value that is associated with each volume image data element or voxel in the reconstructed 3-D volume image. The code values for CT images are often, but not always, expressed in Hounsfield units (HU).

In the context of the present disclosure, the object that is being imaged by CBCT or other type of x-ray system may be equivalently termed the "subject" or the "imaged subject". For medical or dental imaging applications, the object or subject may be a human being.

In the context of the present invention, the terms "digital sensor" and "digital detector" are considered to be equivalent. These describe the panel that obtains image data in a digital radiography system. The term "revolve" has its conventional meaning, to move in a curved path or orbit around a center point. The term "energy band" has its conventional meaning, as referring to a continuous segment of the x-ray energy spectrum.

Figure 2B:
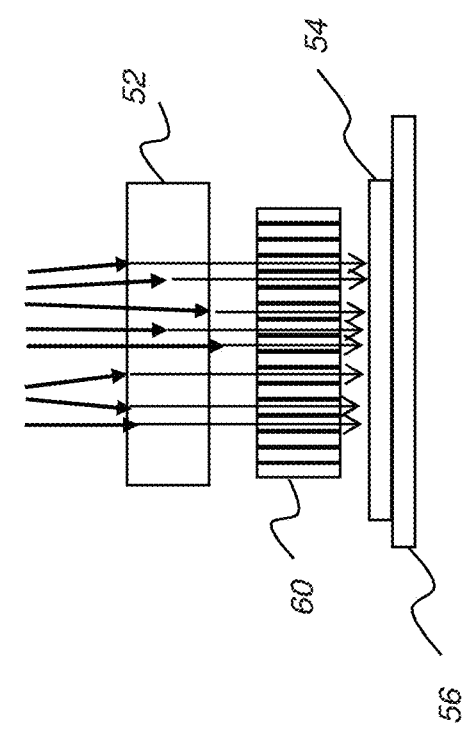
FIG. 2B is a schematic view that shows a digital detector using a scintillator with a fiber optic array in conventional digital radiographic imaging.

In order to more fully understand aspects of the present invention, it is instructive to consider different approaches used for imaging in conventional practice and to compare these with aspects of imaging according to embodiments of the present invention. FIGS. 2A through 2D schematically illustrate different approaches to radiologic imaging. FIG. 2A shows elements of an x-ray imaging sensor 50 that uses an indirect imaging method for generating image data in response to radiation through a patient or other subject. In this model, x-ray photons are incident on an x-ray converting element 52 that converts the energy from ionizing x-ray radiation to visible light or other light energy. X-ray converting element 52 is commonly referred to as a scintillator. An energy detecting element 54, mounted on a support structure 56, then detects the converted energy, such as using an array of photocells. The photocells can be light-sensitive CMOS (Complementary Metal-Oxide Semiconductor) components formed in an array as a semiconductor chip and providing a signal corresponding to each detected image pixel. Unconverted x-ray photons are trapped in an optical fiber plate.

Figure 2C:
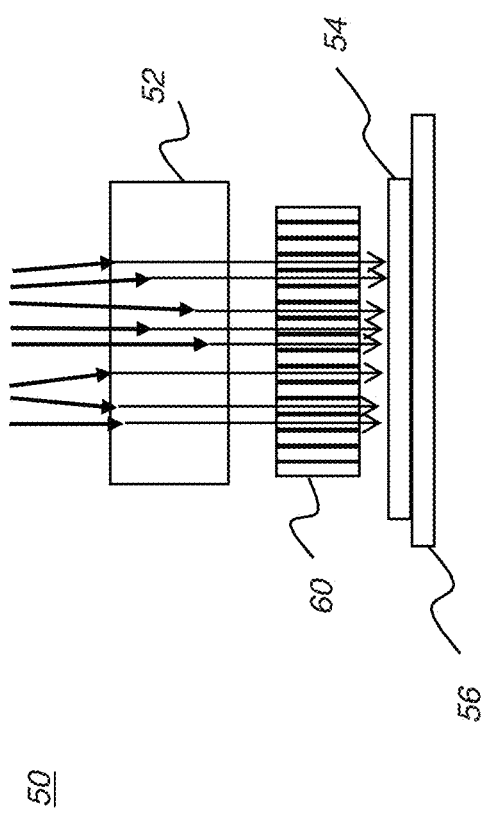
FIG. 2C is a schematic view that shows a digital detector using a thicker scintillator with a fiber optic array in conventional digital radiographic imaging.

Scatter, resulting in cross-talk between pixels and consequent loss of some amount of resolution, is one acknowledged problem with the basic approach shown in FIG. 2A. The modification of FIG. 2B addresses this problem and reduces the number of unconverted x-ray photons by adding a fiber-optic array 60 between the scintillator or x-ray converting element 52 and energy detecting elements 54. FIG. 2C shows another modification that can help to improve sensitivity to radiation, enlarging the width of the scintillator or x-ray converting element 52; however, this solution can result in some loss of sharpness in the obtained image.

Figure 2D:
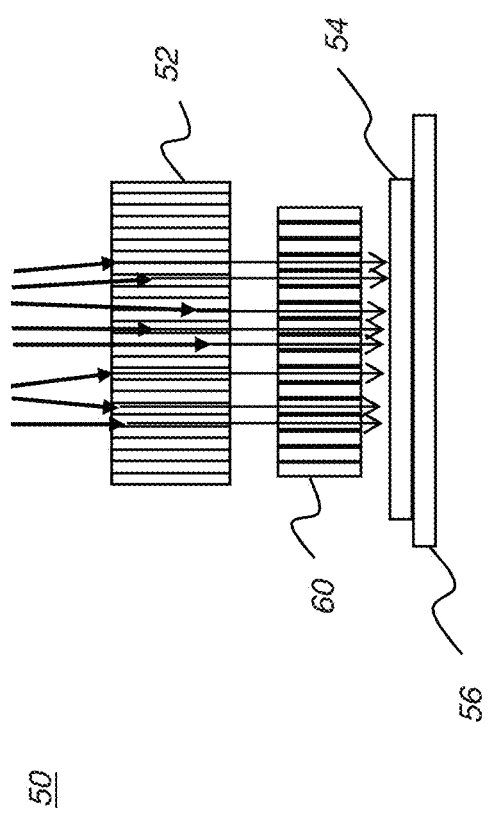
FIG. 2D is a schematic view that shows a digital detector using a structured scintillator with a fiber optic array in conventional digital radiographic imaging.

FIG. 2D shows the use of a structured scintillator serving as x-ray converting element 52. The structured scintillator can use a material such as cesium iodide (CsI), although this material is structurally fragile, expensive and has some limitations with respect to image quality. Some believe that thicker layers of CsI attenuate light faster, such that they produce extra visible-light photons. This modified scintillator type can be used in addition to fiber-optic array 60 as shown in FIG. 2D for some improvement in performance.

The conventional model shown in FIG. 2A and improvements outlined with respect to FIGS. 2B, 2C, and 2D provide a reasonable level of imaging performance for dental imaging applications. However, even with the added cost and complexity of the additional components and features used, only incremental improvements in image quality and overall performance are achieved.

Figure 3:
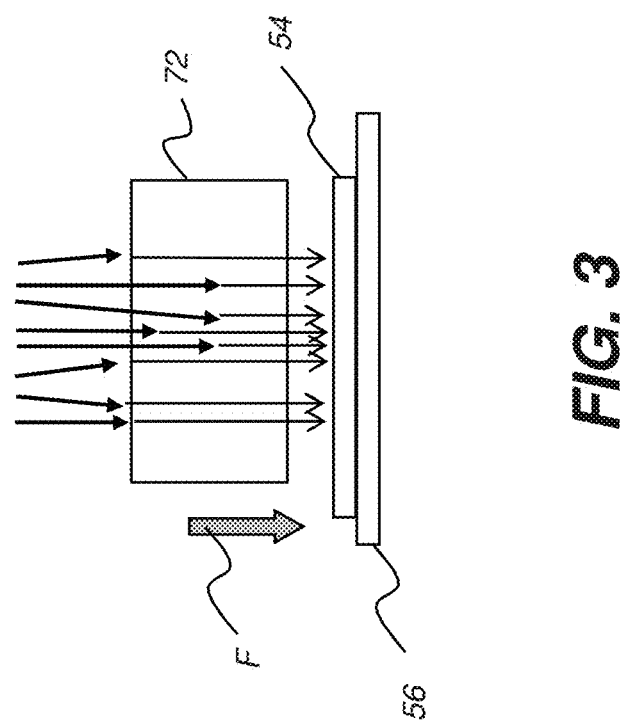
FIG. 3 is a schematic view that shows a digital detector using a photon counting for digital radiographic imaging.

An alternative approach to image capture using a direct imaging method is shown in FIG. 3. An imaging sensor 70 using direct detection has a direct detection element 72, such as a semiconductor or other sensitive material, that converts incident x-ray photons to an electron flow. The excited electrons are then accelerated by an electrical field F and sensed by an electron-sensitive CMOS array that acts as energy detecting element 54. The total energy of the cloud of electrons is representative of the energy of the incident x-ray photon. Advantageously, with direct detection imaging sensor 70, each incoming x-ray photon is much more likely to be detected than with indirect imaging devices. This increases the DQE (detective quantum efficiency), a performance metric for an imaging detector. Reduced scatter, a result of the electric field that guides electron charge toward the CMOS array elements, makes this approach more efficient, improves resolution, and provides a more favorable signal-to-noise (S/N) ratio. As a result, lower levels of ionizing radiation can be used for obtaining an image with direct detection imaging sensor 70 than are needed with the more conventional indirect devices described with reference to FIGS. 2A-2D.

Direct-detection semiconductors used for direct detection element 72 can include polycrystalline or monocrystalline materials. Monocrystalline materials are advantaged over polycrystalline for ease of fabrication and handling; however, there are size constraints to detectors formed from monocrystalline materials. The organized structure of monocrystals guides the propagation of the electrons submitted to an electrical field. Monocrystals are connected to the electron-sensitive CMOS structure by bump bonds.

Figure 4:
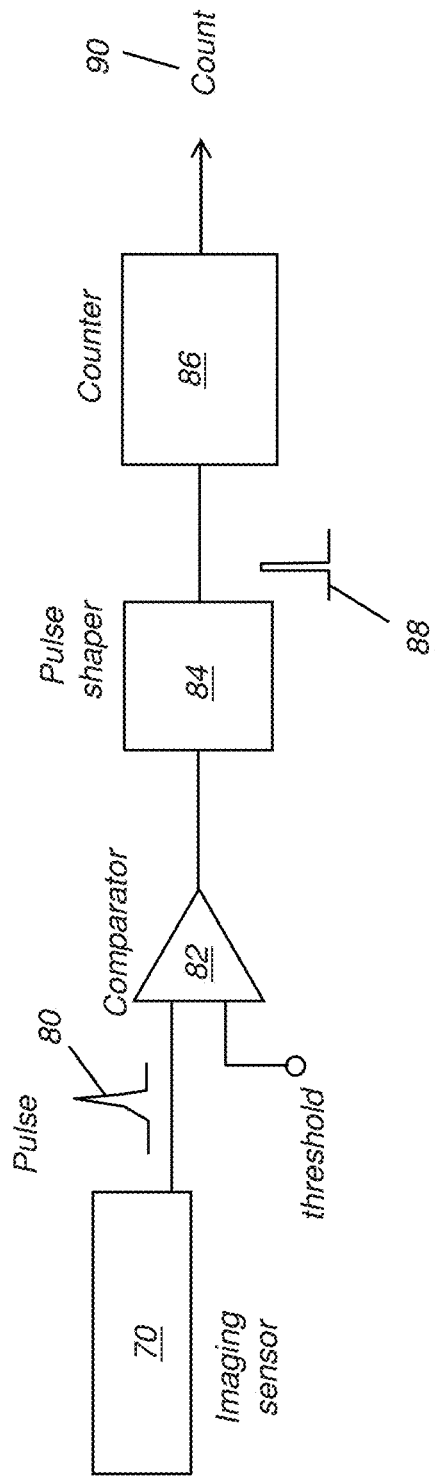
FIG. 4 is a schematic diagram that shows the image processing chain for each pixel of the digital detector when using photon counting.

Another distinction is made between how x-ray detectors record and report the received energy. Integrating x-ray sensors are spatially digitized and provide an analog output that represents the accumulated charge received for each pixel during the exposure. High noise levels can be a problem with integrating sensors. Another approach is commonly termed "photon-counting". In this alternative method, each incoming photon generates a charge, and each of these events is reported or counted. The actual count of photons, or a value computed according to the count, is provided as the image data for each pixel. Advantageously, photon counting has high immunity to noise, provided that pulse strength exceeds background noise levels. FIG. 4 shows the photon-counting sequence in schematic form. An incoming photon generates a pulse 80 at a given energy level. The pulse 80 energy is compared against a threshold value at a comparator 82 and shaped in a pulse shaper 84 to form a shaped pulse 88. A counter 86 then records the pulse event and provides a digital output, a pulse count value 90. A separate pulse count value 90 is obtained for each pixel element in imaging sensor 70. The threshold value can be adjustable or selectable from a range of values, depending on the photon energies of interest. Photon counting x-ray detectors provide suitable performance at low signal level, and therefore allow reducing the x-ray dose given to a patient.

Applicants have recognized that these detector technologies can be combined. For example, combining: (1) Indirect-Detection with Integration, (2) Direct-Detection with Integration, (3) Indirect-Detection with Photon-Counting, and (4) Direct-Detection with Photon-Counting. Indirect-Detection with Integration provides reduced detector cost and scalability. Direct-Detection with Integration provides reduced dose and large-scale detectors. Indirect-Detection with Photon-Counting provides for reduced dose. Direct-Detection with Photon-Counting can provide reduced dose and/or color x-ray.

A further advantage of pulse counting relates to its capability to count pulses 80 at multiple threshold values. Referring to the schematic diagram of FIG. 5, two comparators 82a and 82b are shown for measuring pulse energy. In this particular configuration, a comparator 82a, a pulse shaper 84a, and a counter 86a provide a count 90a value for all pulses above a first threshold; similarly, a comparator 82b, a pulse shaper 84b, and a counter 86b account for only pulses above a higher, second threshold and provide a count 90b accordingly. Simple subtraction then identifies the different power levels achieved for each pulse. It can be appreciated that more than two threshold levels can be measured, using a corresponding arrangement of comparator circuitry, allowing pulse counts at any of a number of threshold values. In addition, thresholds can be selectable, such as adjustable to adjust the response of imaging sensor 70 to various photon energy levels. Thus, for example, an operator can use a set of preset thresholds for differentiating softer from denser tissue in the image that is finally generated.

In addition to setting minimum thresholds, embodiments of the present invention also provide the option of using upper or maximum thresholds for photon energy. This capability can be used for a number of functions, including reducing the generation of excessive noise signals such as from metal artifacts or x-rays passing directly through the direct detection material.

Figure 5:
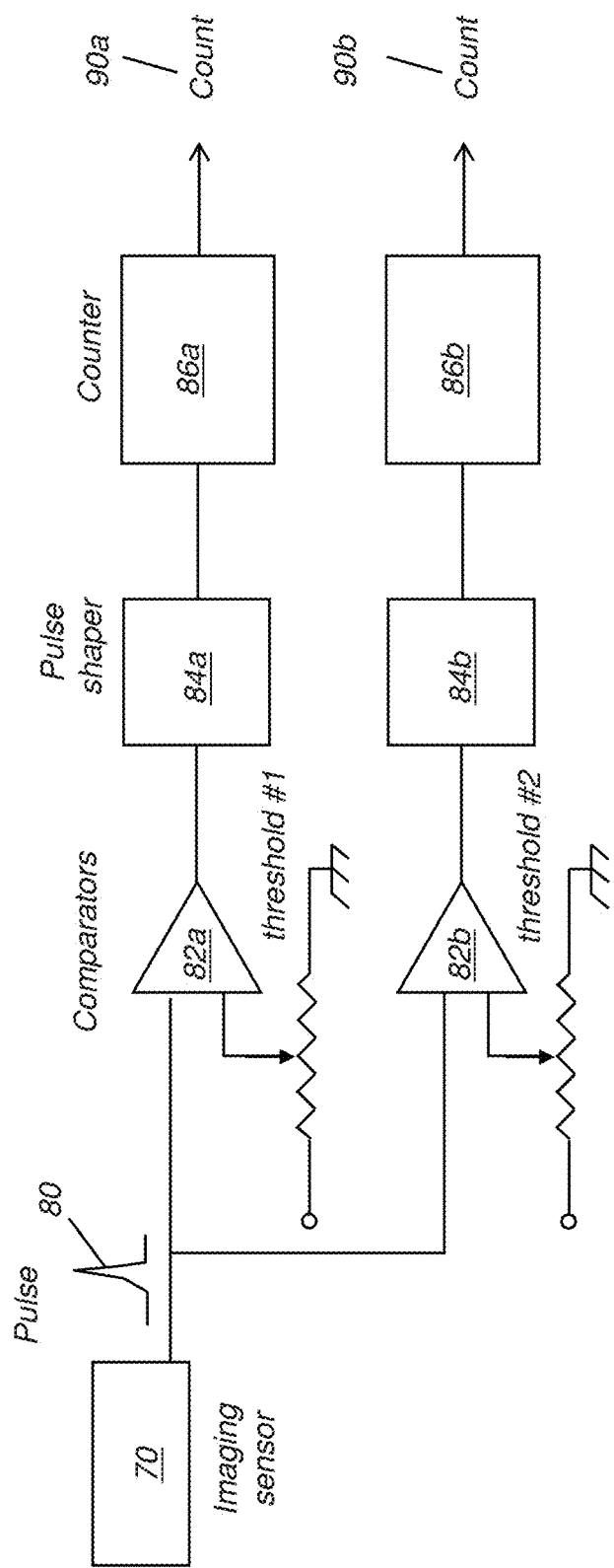
FIG. 5 is a schematic diagram that shows the image processing chain for each pixel of the digital detector using multiple thresholds when using photon counting.
Figure 6A:
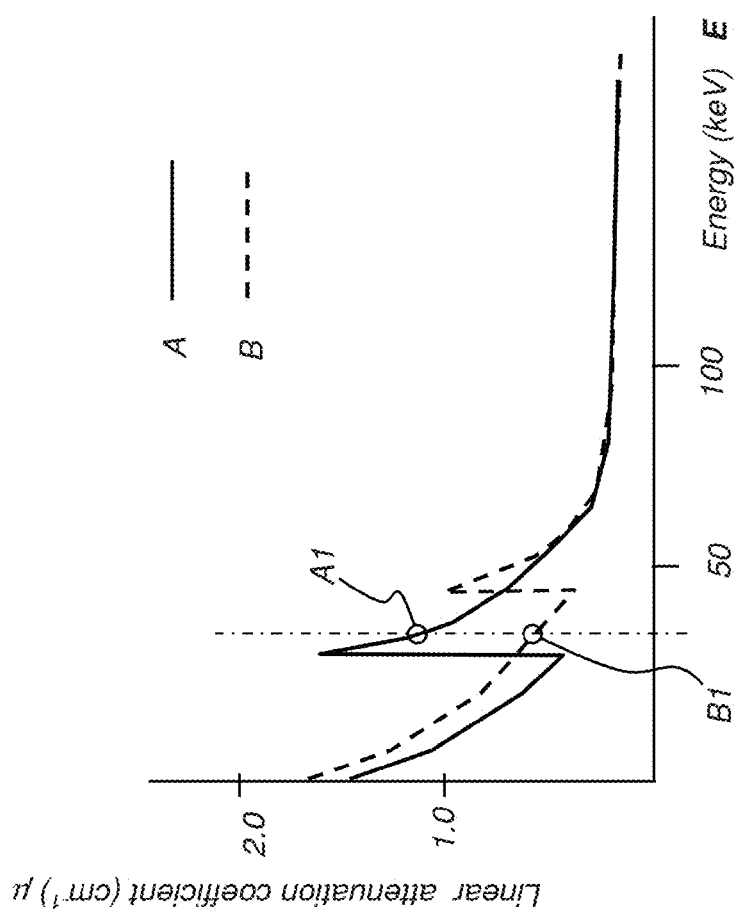
FIG. 6A is a graph that shows linear attenuation characteristics at different energy levels for two exemplary metallic materials.
Figure 6B:
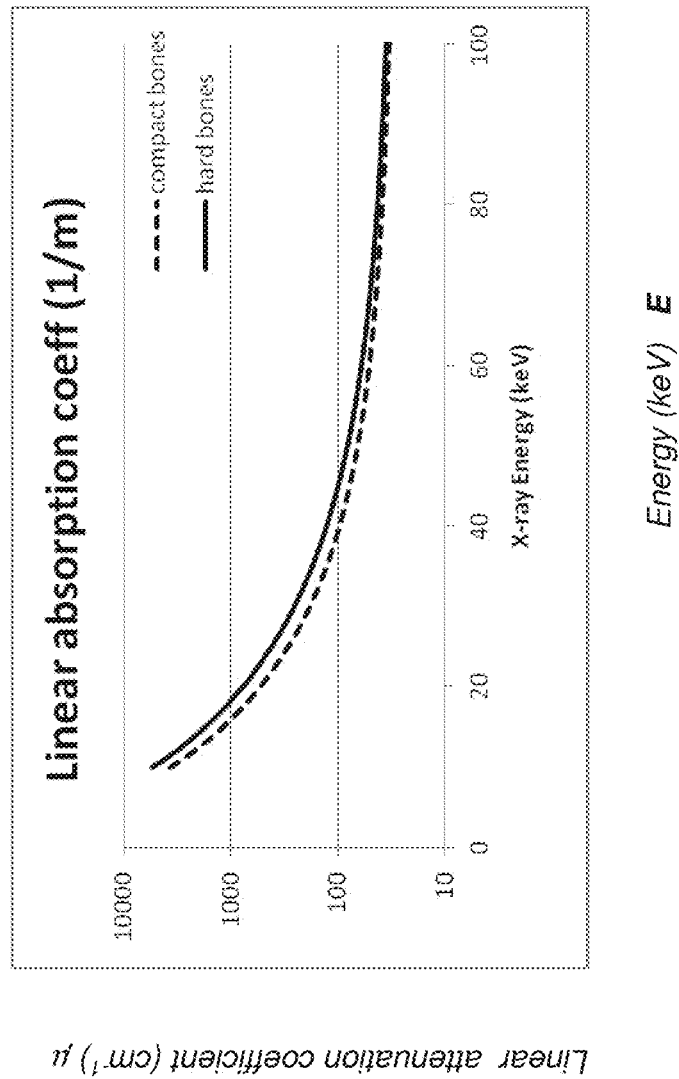
FIG. 6B is a graph that shows the linear absorption coefficient for different types of bone tissue.

The capability to count photons at different energy thresholds, as described with reference to FIG. 5, allows the sensor to differentiate between energy levels obtained from irradiating the subject and provides added dimension to the image data that is provided as a result of each exposure. This capability, described as multi-spectral or "color" x-ray imaging, enables information to be obtained about the material composition of a subject pixel. As shown for typical metals in the simplified graph of FIG. 6A, two materials A and B have different coefficients of attenuation μ that vary with the level of radiation energy, shown as exposure E. At a given exposure, material A attenuates a photon with an energy that corresponds to material A, as shown at value A1. Similarly, radiation impinging on material B attenuates a photon with an energy that corresponds to material B, as shown at value B1. Where photons of these different energy values can be differentiated from each other, it is possible to identify one or both materials in the same pixel or voxel image element of the obtained image. This same basic behavior in response to radiation also allows some measure of capability to differentiate tissue types. By way of example, the graph of FIG. 6B shows relative coefficients of attenuation for different bone densities. As FIG. 6B suggests, different linear absorption characteristics allow differentiation between various types of tissue, such as between bone types.

Color x-ray using photon counting detectors provides for low cost and low dose color x-ray imaging. The use of multispectral or "color" x-ray imaging can have a number of potential benefits of value for dental, ENT, and head imaging. These include minimization of metal artifacts, separate reconstruction of soft and hard tissue, more efficient segmentation algorithms for tooth and bone features, improved pathology detection for cancer and other disease, and detection of trace materials or contrast agents.

In addition to opportunities for improvement in the image processing chain, there are a number of differences in structure, operation, scanning sequence, dimensions, and supporting hardware that are needed to provide the advantages of photon counting in embodiments of the present invention. As one significant difference from conventional large-area image detection, the photon-counting architecture results in an image detector of reduced size, generally requiring a scanning sequence even where only a 2-D image is obtained. For volumetric imaging, such as in the sequence needed for CT or for cone-beam CT (CBCT) imaging, it may be necessary not only to scan within the same plane, but to provide a 3-dimensional helical scan.

Figure 7:
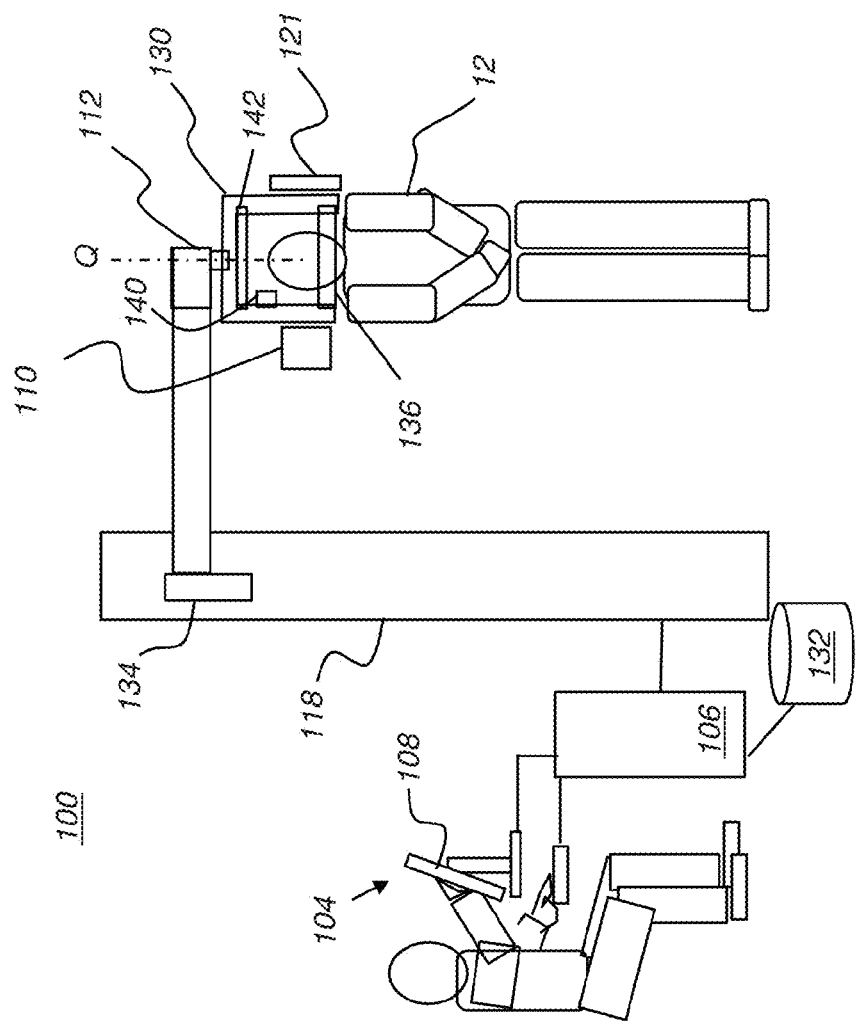
FIG. 7 is a schematic diagram showing an imaging apparatus for imaging portions of the patient's head using photon counting.

The schematic diagram of FIG. 7 shows an imaging apparatus 100 for 2-D imaging, such as panoramic imaging, in which a succession of two or more 2-D images is obtained and images of adjacent content are arranged to form a larger image, or for 3-D imaging, such as tomography, computed tomography volume imaging, or cone beam computed tomography (CBCT) imaging in dental, ENT, and related head imaging applications. A rotatable mount 130 is provided on a column 118, preferably adjustable in height to suit the size of patient 12. Mount 130 maintains x-ray source 110 and a radiation sensor 121 on opposite sides of the head of patient 12 and, optionally, rotates to orbit source 110 and sensor 121 in a scan pattern about the head, obtaining a projection image at each angle in a set of projection angles. Mount 130 rotates about an axis Q that corresponds to a central portion of the patient's head, so that its attached components orbit about the head. Sensor 121, a photon-counting sensor according to an embodiment of the present invention, is coupled to mount 130, opposite x-ray source 110 that emits a radiation pattern suitable for 2-D imaging, for tomosynthesis imaging, or for CT or CBCT volume imaging. An optional head support 136, such as a chin rest or bite element, provides stabilization of the patient's head during image acquisition. A computer 106 has an operator interface 104 and a display 108 for accepting operator commands and for display of volume images obtained by imaging apparatus 100. Computer 106 is in signal communication with sensor 121 for obtaining image data and provides signals for control of source 110 and, optionally, for control of a rotational actuator 112 for mount 130 components. One or more height sensors 134 is also sensed by computer 106 in order to obtain an initial height setting and to track relative vertical displacement of the sensor 121 relative to the patient's head during the helical scan. Computer 106 is also in signal communication with a memory 132 for storing image data. An optional alignment apparatus 140 is provided to assist in proper alignment of the patient's head for the imaging process. Alignment apparatus 140 includes a laser that provides one or more line references for head positioning according to an embodiment of the present invention. In alternate embodiments, alignment apparatus 140 includes a visible light beam or other marker, or a mechanical or other positioning apparatus. Imaging apparatus 100 may also have the capability for panoramic or cephalometric imaging using x-ray source 110 and sensor 121 or other imaging sensor.

There can be a number of variable scan patterns according to the type of imaging that is required. Tomosynthesis, for example, typically uses a scan that is less than 180 degrees about the patient. CBCT scanning may require a helical scan pattern with one or more revolutions about the patient's head. An optional adjustment mechanism 142 is provided for adjusting the source-to-image (SID) distance between the x-ray source 110 and sensor 121 to suit the scan pattern for different patients or types of imaging.

One drawback of typical photon-counting image detectors is their relatively small size. Unlike a conventional digital radiography imaging panel that has an array with hundreds of elements in the height and width directions, the photon-counting sensor is typically of smaller size, with a width that may be fewer than 100 pixels in dimension. This problem can be addressed by tiling, an approach in which multiple image detectors are combined to cover a larger detection area. The use of polycrystalline materials, as opposed to conventional monocrystalline detector materials as noted earlier, can also help to provide larger detectors.

Figure 8:
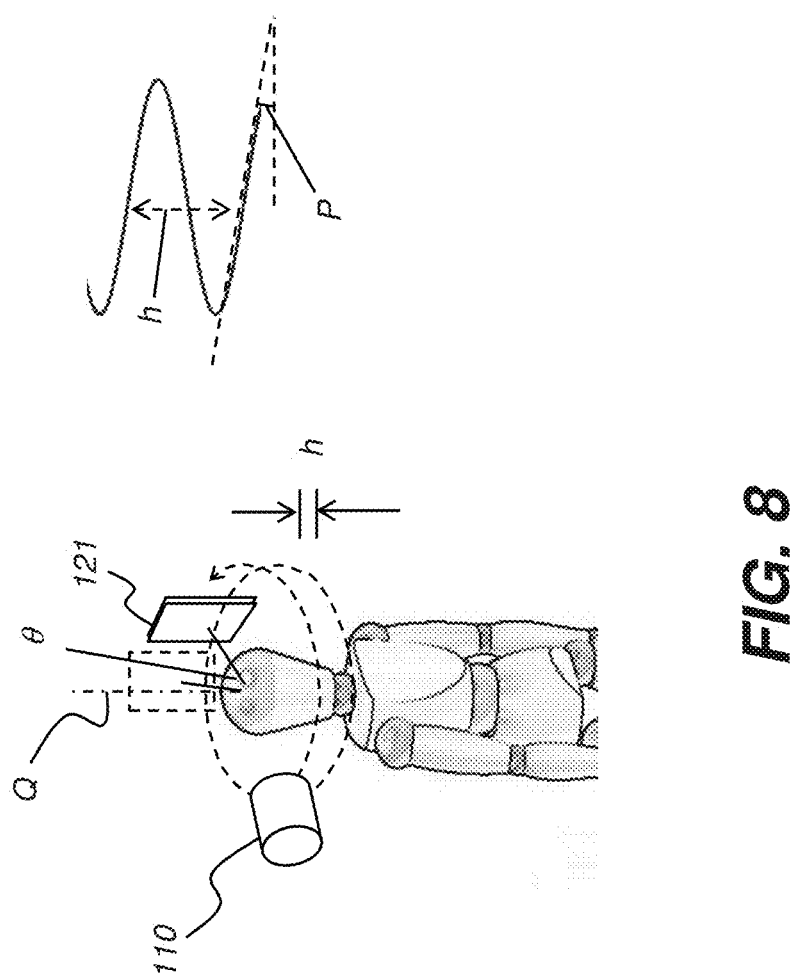
FIG. 8 is a schematic diagram that shows a portion of a helical scan for the digital sensor and radiation source.

Another solution for the size constraints of photon-counting image detectors adapts their scanning sequence to effectively increase the field of view. In practice, this size limitation requires a different scanning sequence from that used for conventional CBCT imaging. A helical scan can be used to acquire the needed image data for volume imaging. In operation, mount 130 rotates about the head of patient 12 multiple times, thereby scanning sensor 121 about patient 12 in a helical orbit, as is shown in FIG. 8. In FIG. 8, an adjacent imaging position is shown in dotted outline, with the angular distance exaggerated for clarity. According to an embodiment of the present invention, the vertical height h change of the helix during revolution of the source and detector, which can also be expressed in terms of the helical pitch angle P, and angular change θ between successive image acquisitions, is adjustable.

The helical scan needed for CBCT imaging using a photon-counting sensor 121 can be provided following either of a number of scanning apparatus models. FIGS. 9A and 9B show a first approach to this problem, in which mount 130 that contains sensor 121 and source 110 is itself coupled to a movable travel arm 128 that is vertically translated during the scan, displaced by an actuator 122 during rotation of mount 130. This translation changes the relative vertical position of the imaging sensor and the radiation source to the patient's head during the helical scan. In one embodiment for the helical scan, an imaging sensor can be a slit shaped sensor with the longest dimension configured to extend during the scan in a direction that is perpendicular to the helix axis.

Figure 10A:
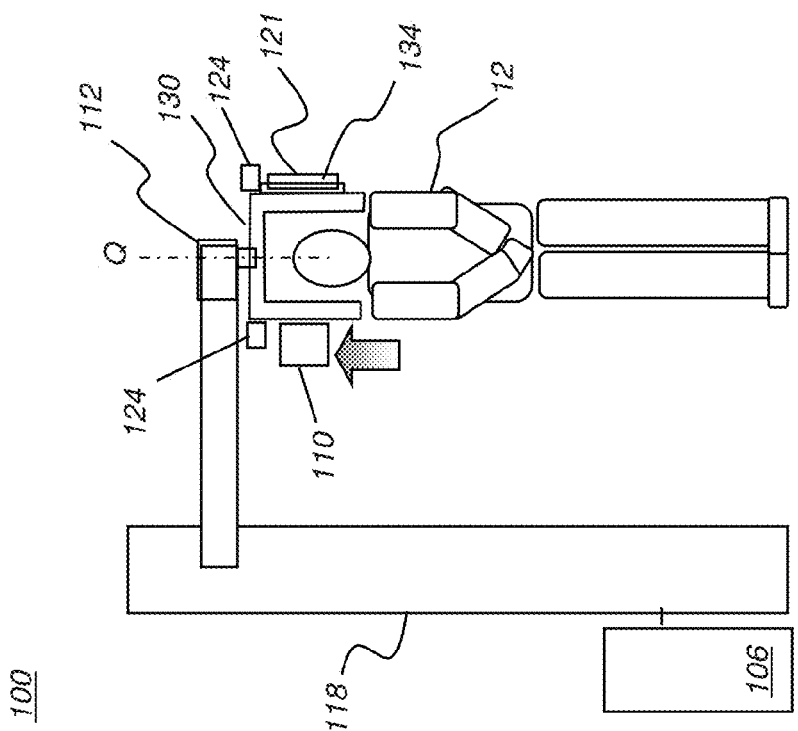
FIGS. 10A and 10B show the imaging apparatus that provides a helical scan by changing the elevation of the digital sensor and radiation source during revolution about the patient.
Figure 10B:
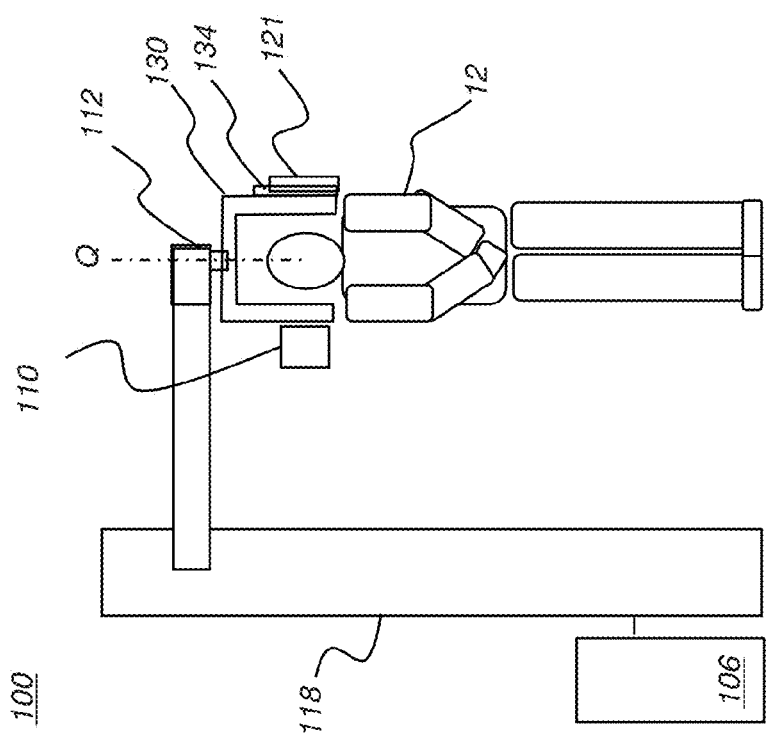

FIGS. 10A and 10B show a second approach to this problem, in which mount 130 itself has the same height, while source 110 and sensor 121 are vertically translated during the helical scan, thereby changing the relative vertical position of the imaging sensor and the radiation source to the patient's head during the helical scan. FIGS. 11A and 11B show a third approach to this problem, in which mount 130 itself has the same height, while a vertically adjustable platform 138 is used as an actuator to provide relative movement between the head of the patient and source 110 and sensor 121 for changing the relative vertical position of the imaging sensor and the radiation source to the patient's head during the helical scan.

As shown in FIGS. 9A-11B, one or more actuators 124 within mount 130, or other height adjustment devices provide this vertical translation function as source 110 and sensor 121 revolve about the patient's head. Computer 106 coordinates and tracks the vertical and rotational or angular movement and corresponding actuators needed for helical scanning. Sensor 134 provides feedback information on height with the FIG. 9A/B, FIG. 10A/B and FIG. 11A/B scan configurations.

Operation Sequence

Figure 12:
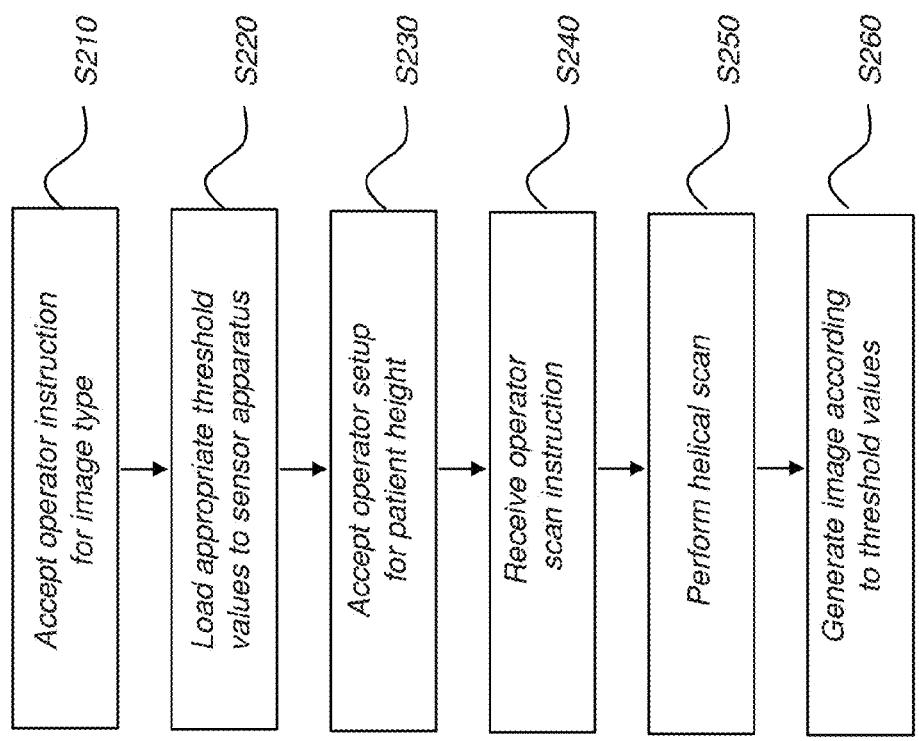
FIG. 12 is a logic flow diagram showing steps for image acquisition according to an embodiment of the present invention.

The logic flow diagram of FIG. 12 shows an operational sequence for CBCT scanning of the head according to an embodiment of the present invention, for the imaging apparatus shown in FIGS. 7, 9A, 9B, 10A, 10B, 11A, and 11B. In an accept instruction step S210, the imaging apparatus accepts operator instructions related to the type of image to be obtained, which may include information on the types of tissue that are of particular interest. In a threshold setup step S220 an appropriate set of threshold values and other operational parameters is loaded to circuitry of sensor 121. An operator setup step S230 allows the operator to adjust mount 130 components to suit the height of the patient and size of the patient's head. This registers an initial height setting that provides information for subsequent helical scan execution. The operator can also use head support 136 and alignment apparatus 140 to adjust patient position. An instruction entry step S240 accepts the operator instruction to begin the scan sequence and to execute a scan and acquisition step S250. During step S250, multiple 2-D images are obtained at successive rotational and height positions for acquiring the CBCT scan data. An image generation step S260 then forms the 3-D volume image from the obtained 2-D images, using an image reconstruction algorithm, such as one of the filtered back-projection routines well known in the volume imaging arts. The resulting image is then displayed for viewing by the practitioner and the image data is stored in memory 132 (FIG. 7) or other memory circuitry that is accessible to computer 106.

According to an embodiment of the present invention, the tissue type of interest dictates the set of operational parameters that are most suitable for imaging a particular patient. By way of example, and not by way of limitation, Table 1 lists a set of parameters that are loaded when the operator elects to generate an image for tissue type A. Table 2 lists alternate example parameters for generating an image for tissue type B. As described earlier with respect to FIG. 8, the pitch of the helical scan pattern can be specified in terms of vertical translation or helical pitch angle P. The helical pitch angle P can be varied from 0 degrees (that is, a slope of 0) to 40 degrees or more and is based on the relative size of the sensor 121 and the amount of overlap needed between successive images.

It can be appreciated that some modification of procedures listed and described with reference to FIG. 12 are similarly used for other types of imaging using imaging apparatus 100, with appropriate changes for the scan pattern and number of images obtained. For panoramic or tomosynthesis imaging, for example, a full scan is not needed. Only a partial scan is needed, with the scan orbit defined within a single plane, rather than helical as described for CBCT scanning.

TABLE 1

Operational Parameters for Tissue Type A

| Parameter | Setting |
| --- | --- |
| Radiation energy level | 30 kVp |
| Threshold values to sensor | +1.23 V |
|  | +1.41 V |
| Image acquisition interval | every 0.8 degrees |
| Vertical translation between images | 0.1 mm |

TABLE 2

Operational Parameters for Tissue Type B

| Parameter | Setting |
| --- | --- |
| Radiation energy level | 40 kVp |
| Threshold values to sensor | +1.02 V |
|  | +1.34 V |
| Image acquisition interval | every 0.9 degrees |
| Vertical translation between images | 0.12 mm |

As noted earlier with respect to FIG. 5, different types of materials have different photon energy "signatures", enabling the volume scan to detect two or more different materials in the imaged subject. This feature enables the same imaging apparatus to be employed for obtaining different information using the same scanning pattern. According to an embodiment of the present invention, different sets of threshold settings are provided, depending on the nature of the volume image that is desired. One set of threshold settings, for example, is optimized for obtaining information on teeth, while another set of threshold settings works best for imaging gum and underlying support structures. Still another set of threshold settings provides the best conditions for imaging of the throat, ear, or nasal passages, with corresponding elevation adjustments. As described with reference to FIG. 12, an appropriate set of threshold values is selected and loaded to the image acquisition circuitry of the imaging sensor according to the type of imaging that is to be performed and to the type of tissue that is of particular interest for a patient.

Embodiments of the present invention have been described for imaging various regions of the head and upper body of a patient using an extra-oral detector. The apparatus of the present invention can be used, for example, to obtain a full-mouth series (FMS) in dental practice. It should be noted that sensor 121 (FIG. 7) can combine photo-counting circuitry with other, conventional imaging components, such as with indirect detection or integrating imaging components described earlier with reference to FIGS. 2A-D. Multiple sensors 121 can be coupled together to increase the area over which an image is obtained for each x-ray exposure. The photo-counting sensor 121 can be used to support different imaging modes, including CT or CBCT, panoramic, or cephalometeric imaging. CT and CBCT imaging modes obtain a volume image from multiple 2-dimensional (2-D) images. Panoramic and cephalometeric imaging are 2-dimensional imaging modes that may require scanning of sensor 121 in one or two directions within the same imaging plane during imaging in order to cover the full imaging area.

With the necessary adaptations to hardware and to the scanning patterns that are used, embodiments of imaging apparatus 100 (FIG. 7) are capable of a number of types of imaging, including 2-D imaging and panoramic imaging, tomosynthesis imaging, and volume imaging using computed tomography (CT) or cone-beam computed tomography (CBCT).

Tomosynthesis is an imaging type that takes advantage of the capability of systems such as imaging apparatus 100 to localize focus over some portion of an arc and to process the resulting image data in order to provide an image that provides some amount of depth information from a series of individual 2-D images obtained at different angles along the arc. Tomosynthesis thus provides a type of volume image, formed from a sequence of two-dimensional (2-D) images. Basic principles for dental tomosynthesis are described, for example, in U.S. Pat. No. 5,677,940.

Figure 13:
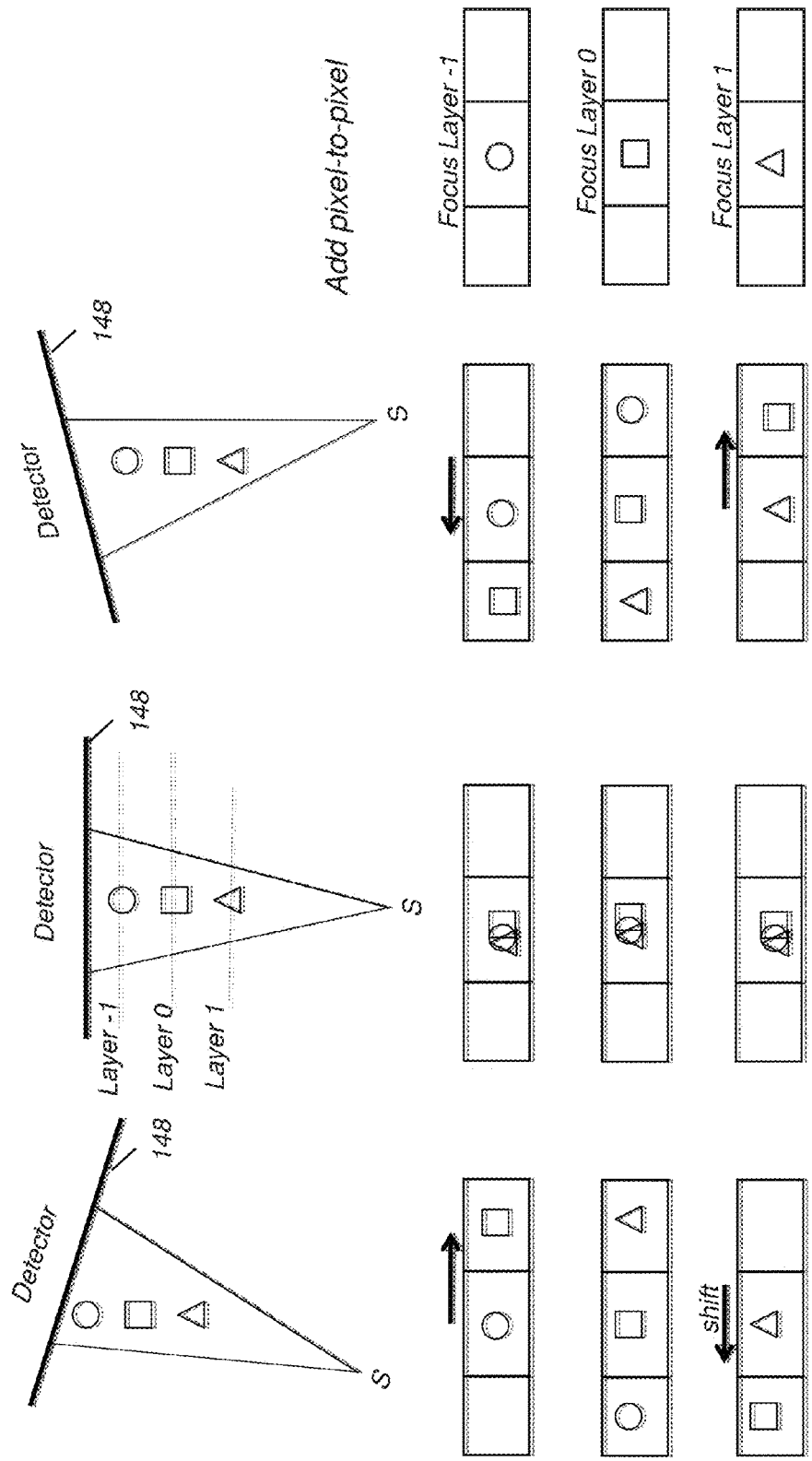
FIG. 13 is a schematic diagram that shows features of image acquisition and processing for tomosynthesis according to an embodiment of the present invention.
Figure 14:
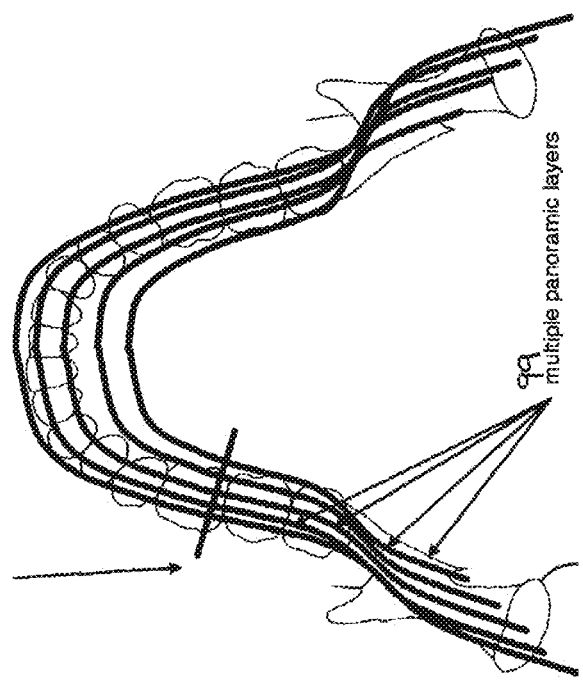
FIG. 14 is a top view diagram that shows example panoramic layers within the dental arch for a patient.

The schematic diagram of FIG. 13 shows how tomosynthesis operates to obtain images at different focus layers. Radiation from a source S is directed through an object, shown in FIG. 13 as one of a set of geometric shapes in different focal planes, to a detector 148. Layers are indicated as layer −1, layer 0, and layer 1. Source S or detector 148 travel in an arc, as shown during image acquisition. Images on one tomosynthesis plane or layer are combined with corresponding images in the sequence with objects in images from other tomosynthesis layers, such as by straightforward addition of pixels, in order to provide a combined volume image. As the radiation source and sensor are positioned on opposite sides of the patient's head, a number of bony structures are superimposed within the individual 2-D images that are obtained. For example, it can be difficult to differentiate incisors from spine or molars from other structures along the dental arch, as shown in FIG. 14. Superimposed images used for tomosynthesis, with successive images obtained at different angles, allow reconstruction of the underlying features and retrieval and representation of the proper depth information. This technique allows obtaining a best focus layer at a preset position and with a preset speed profile and collimation setting. As pixels are added in combination, bony structures lying outside of the layer of best focus tend to blur, without degrading the visualization of bony structures that lie within the region of interest. By way of example, FIG. 14 shows multiple panoramic layers 99 along the dental arch.

One drawback of this technique relates to the discrepancy that can occur between the focus layer and the actual region of interest, such as the patient's teeth. This can occur even when the locus of the rotation axis is predefined for a given region along the dental arch or other structure. However, this disadvantage can be remedied by permitting the choice of a best focus layer that is different from the preset layer and by adapting the position of this best focus layer relative to the shape of the patient's dental arch. In processing, a shift of pixels within each image is performed, the amplitude of the shift chosen so that the position of the anatomical structure of interest is located, after shifting, at the same position on each image. After a pixel-to-pixel adding process of the plurality of acquired images, a final image is obtained in which the anatomical structure of interest is located in the focus layer and other structures are blurred (resulting in horizontal stripes, for example). By repeating the process with other shift amplitudes values, a plurality of focus layers can be obtained and the best one can be chosen for a region of interest. Among advantages of this technique can be image quality, which is only slightly dependent upon the positioning of the patient.

In alternate exemplary embodiments, a photon-counting sensor is used as an intraoral sensor. It can be appreciated that a number of modifications to related art photon counting sensors are required for this purpose. One difficulty relates to resolution requirements for intraoral imaging. Extraoral imaging sensors have relatively large pixel sizes compared with pixel sizes for the resolution needed for intraoral imaging. Typical pixel sizes for extraoral imaging sensors can be on the order of 100 microns or more; intra-oral imaging requires resolution on the order of 20 microns or less. At the same time, 8-bit or better depth resolution is needed, requiring considerable support circuitry for digital counters associated with each pixel. To address the need for higher resolution and/or sufficient bit depth for intraoral dental imaging, exemplary embodiments herein can employ an alternate methods/apparatus for counting photon events, by using an analog photon counting device (e.g., analog charge storage device) to reduce support circuitry included in the digital counters associated with each pixel. In one embodiment, the support circuitry (e.g., transistors) can be reduced by a factor of 2×, 5× or 10×. For each radiation photon (e.g., x-ray) that is received, the resulting electron cloud can generate a pulse or cause a charge (e.g., preset charge) to be stored in a capacitor or other analog storage device. In one embodiment, a lower threshold can be used to reduce or eliminate storing charge in the capacitor for noise or erroneous events (e.g., scatter). Over time, the amount of charge (that is, current, voltage) that is stored in the analog storage device is indicative of the number of photons received for the corresponding pixel. For example, analog-to-digital circuitry senses the stored charge and provides an output digital value that indicates the photon count for the pixel. In one embodiment, a plurality of analog photon counting devices can be provided for each imaging pixel to support a plurality of thresholds to implement pulse counts for a number of threshold values even for the reduced imaging pixel size of the intra-oral digital sensor.

Other changes for intraoral use include thinning of direct detection element 72 (FIG. 3). This helps to reduce the amount of radiation needed and/or allows lower voltage levels to be used to attract the electron cloud toward energy detecting elements 54. At the same time, radiation-hardening can be used needed to help protect energy detecting elements 54 that sense the resulting electron cloud from direct detection element 72. In addition, because some photons can escape without interaction with direct detection element 72, the use of an additional upper threshold can reduce or alleviate noise effects from these photons. A voltage condition (e.g., transient) above this upper threshold is thus not counted. Both lower and upper threshold conditions can be used to effectively validate the photon count. The lower threshold can reduce noise effects; the upper threshold can reduce the effects of radiation (e.g., photons) directly on detector circuitry. In one embodiment, a plurality of thresholds can be implemented in between the lower threshold and the upper threshold to provide detection of materials of different characteristics in the head of the patient. For example, the plurality of thresholds can be used to differentiate soft tissue and bone, and/or to identify and remove or reduce metal artifacts in the dental imaging system diagnostic image of the patient. Additional lead shielding is also provided behind the intraoral detector to reduce any stray radiation from passing through the detector.

In one exemplary embodiment for an analog photon counting device included in a digital counter, each energy cloud of electrons, which result from a radiation photon, received by an intraoral sensor imaging pixel can result in a pulse being generated by the intraoral sensor imaging pixel. The pulse can be used to increment a counter. Alternatively, the pulse can be used by the intraoral sensor imaging pixel to implement a preset electric charge that can be used for analog photon counting over the radiation interval. For example, the preset electric charge can be stored (e.g., integrated or counted) into an analog storage device for each pulse for each intraoral sensor imaging pixel during the radiation interval. Then, photon counting can be determined by dividing a total stored charge for the radiation interval in the analog storage device by the preset electric charge. Alternative embodiments for analog photon counting in the digital detectors for intraoral sensors can be used. Further, a plurality of analog photon counting devices can be included in a digital counter for each intraoral sensor imaging pixel to implement a plurality of thresholds or a plurality of ranges (e.g., a first threshold, a second threshold, a third threshold, responsive to a first range of photon energy, responsive to a second range of photon energy, etc.) to differentiate a plurality of materials in a dental diagnostic image or to implement low dose and/or multi-spectral or "color" x-ray imaging in dental intraoral photon counting direct sensor imaging systems/methods.

Intraoral applications using photon counting detectors can be 2D intraoral imaging and 3D intraoral imaging. 2D intraoral imaging includes individual images of patient's teeth/mouth using an intraoral detector. 3D intraoral imaging includes multiple images of patient's teeth/mouth using an intraoral detector, and combining these images into 3D representation. This has been referred to as chair-side cone beam CT. Chair-side cone beam CT allows a dental practitioner to obtain a 3D image without moving/transporting a patient to a full 3D imaging station/equipment during a surgical procedure.

It should be noted that extra-oral embodiments of the present invention can also provide an analog count, rather than using a digital counter arrangement. The accumulated analog charge, incremented once for each photon, can be distinguished from conventional types of integrated radiation detection that provide a digital value according to the relative brightness of each pixel in the scintillator.

Consistent with an embodiment of the present invention, a computer executes a program with stored instructions that perform on image data accessed from an electronic memory. As can be appreciated by those skilled in the image processing arts, a computer program of an embodiment of the present invention can be utilized by a suitable, general-purpose computer system, such as a personal computer or workstation, as well as by a microprocessor or other dedicated processor or programmable logic device. However, many other types of computer systems can be used to execute the computer program of the present invention, including networked processors. The computer program for performing the method of the present invention may be stored in a computer readable storage medium. This medium may comprise, for example; magnetic storage media such as a magnetic disk (such as a hard drive) or magnetic tape or other portable type of magnetic disk; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

It should be noted that the term "memory", equivalent to "computer-accessible memory" in the context of the present disclosure, can refer to any type of temporary or more enduring data storage workspace used for storing and operating upon image data and accessible to a computer system. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing processes and for recording entered values, such as seed points, or storing intermediate and final results of calculations and other processing. Computer-accessible memory can be volatile, non-volatile, or a hybrid combination of volatile and non-volatile types. Computer-accessible memory of various types is provided on different components throughout the system for storing or recording, processing, transferring, and displaying data, and for other functions.

A first example embodiment can provide a dental imaging apparatus for obtaining an image from a patient, the apparatus comprising a radiation source; a digital imaging sensor that provides, for each of a plurality of image pixels, at least a first digital value according to a count of received photons that exceeds at least a first energy threshold, wherein the imaging sensor comprises a direct-detection material that converts incident x-ray photons to an electron flow; a mount that supports at least the radiation source; and a computer in signal communication with the digital imaging sensor for acquiring one or more two-dimensional images. In one example, the dental imaging apparatus can be an extra-oral dental imaging apparatus or an intra-oral dental imaging apparatus. In one embodiment, the dental imaging apparatus can be an extra-oral dental imaging apparatus or an intra-oral dental imaging apparatus.

A second example embodiment can provide a dental imaging apparatus for obtaining an image from a patient, the apparatus comprising a radiation source; a digital imaging sensor that provides, for each of a plurality of image pixels, at least a first digital value according to a count of received photons that exceeds at least a first energy threshold, wherein the imaging sensor comprises mercuric iodine (e.g., HgI2) to convert incident x-ray photons to an electron flow; a mount that supports at least the radiation source; and a computer in signal communication with the digital imaging sensor for acquiring one or more two-dimensional images. In one embodiment, the dental imaging apparatus can be an extra-oral dental imaging apparatus or an intra-oral dental imaging apparatus.

A third example embodiment can provide an intra-oral dental imaging apparatus for obtaining an image from a patient, the apparatus comprising a radiation source; a digital imaging sensor that provides, for each of a plurality of image pixels, at least a first digital value according to a count of received photons that satisfy at least a first energy threshold; and a computer in signal communication with the digital imaging sensor for acquiring one or more two-dimensional images. The intra-oral dental imaging apparatus can include an alignment system to align the radiation source to the digital imaging sensor, where the alignment system can be mechanical, electromechanical or optical. The intra-oral dental imaging apparatus can include a mount that supports the radiation source. The intra-oral dental imaging apparatus can include a second digital value according to a count of received photons that satisfy a second energy threshold for each of the plurality of image pixels.

A fourth example embodiment can provide an method of operating an intra-oral dental imaging system for obtaining image data of at least a portion of a patient's head, the method comprising providing a digital imaging sensor that provides, for each of a plurality of image pixels, at least a first digital value according to a count of received photons that satisfy at least a first energy threshold; obtaining a set of values that relate to one or more of an exposure energy level; orienting a radiation source to the digital imaging sensor; acquiring a plurality of digital images according to the obtained set of values; and generating and displaying a diagnostic image formed from the plurality of acquired digital images.

A fifth example embodiment can provide an imaging apparatus for obtaining a volume image of at least a portion of a patient's head, the apparatus comprising a rotatable mount comprising a radiation source and a digital imaging sensor and coupled to a rotational actuator that is energizable to revolve the imaging sensor and source in a scan pattern about the patient's head; and a computer in signal communication with the digital imaging sensor for acquiring a plurality of two-dimensional images at successive positions along the scan pattern; wherein the imaging sensor provides, for each of a plurality of image pixels, a digital value according to a count of received photons that exceed at least one energy threshold. The imaging apparatus can include one or more vertical actuators energizable for changing the relative vertical position of the imaging sensor and the radiation source to the patient's head during the revolution.

Example imaging apparatus embodiments can include polycrystalline materials or monocrystalline materials, wherein the polycrystalline materials or monocrystalline materials comprise cadmium telluride (CdTe or CadTel), lead iodine (PbI), lead oxide (PbO), and mercuric iodide (HgI2) for the digital imaging sensor.

Example imaging apparatus embodiments can include each imaging pixel configured to generate a pulse for each received photon that exceeded the at least one energy threshold, where a clock is incremented by the pulses.

Example imaging apparatus embodiments can include the imaging sensor configured to provide an upper threshold, wherein the each imaging pixel outputs a first pulse for a received photon that is above the first energy threshold and is less than the upper threshold, and wherein the each imaging pixel outputs a second pulse for a received photon that is above a second energy threshold and is less than the upper threshold, wherein a prescribed electric charge is generated for said each first and second pulse. Alternatively, a first photon counting is determined by dividing a first total electric charge responsive to the first pulses by a prescribed electric charge relative to one first pulse, and wherein a second photon counting is determined by dividing a second total electric charge responsive to the second pulses by a prescribed electric charge relative to one second pulse. In one embodiment, the first and second pulses are mutually exclusive.

The capability to differentiate between two or more energy bands, possible when using a photon counting detector or other type of energy resolving detector, can help to provide additional information on the material content of the scanned object. The standard 3-D volume reconstruction from a CBCT system, without the added value of photon counting or other energy resolution, provides only an effective attenuation coefficient $\mu_{eff}$ for each reconstructed image voxel. This is a single value, averaged over each angle over which the data for the voxel is obtained. This gives a single point of data, making it difficult to accurately infer the type of material or materials that the voxel comprises. In one embodiment, two or more energy bands are essentially non-overlapping.

In order to more accurately determine the material composition of the voxel, two or more points of data are helpful. This is because the attenuation characteristic for a material, considered over a range of energy levels, is fairly linear, with characteristic levels and slope for any material type. Since two points define a line and its slope, it is most useful to acquire two attenuation values, one at each of two different energy levels. For this capability to be realized, the X-ray attenuation coefficient must be calculated at two or more monochromatic energies at a 3D array of points in the object. Certain exemplary embodiments described herein include, but are not limited to iterative reconstruction methods and/or apparatus that enable the monochromatic X-ray attenuation coefficient to be more accurately calculated at two or more X-ray energies within the object, using an energy resolving detector.

Figure 15:
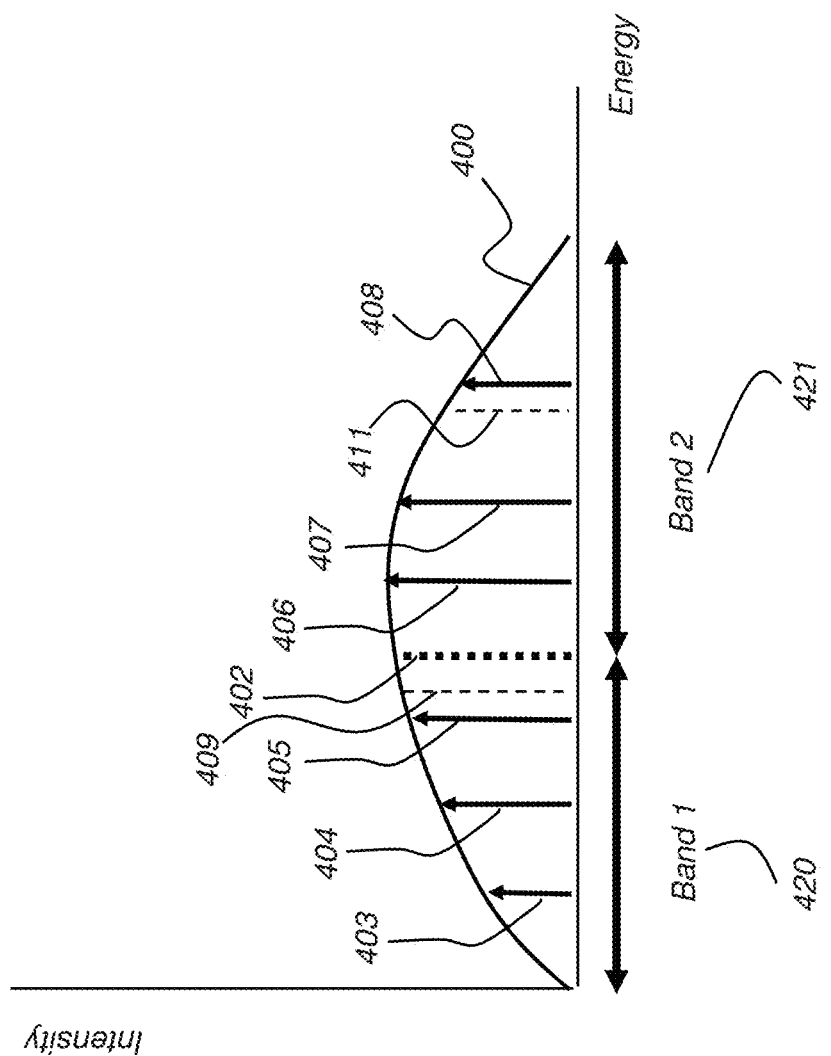
FIG. 15 is a graph that shows spectral content for two different spectral bands.

An exemplary embodiment for a photon counting system with two or more resolved photon energy bands is described with reference to FIGS. 15 and 16. FIG. 15 shows the spectral intensity distribution 400 of the filtered polychromatic X-ray source that is incident on the object, with relative intensity plotted against energy (wavelength). The spectral content may vary somewhat with direction, but for the purpose of the description, it can be assumed that the spectrum of the filtered X-ray source is essentially or substantially isotropic. The energy spectrum is divided into two bands 420 and 421. For the purpose of the present description, the case of only two energy bands is considered. However, exemplary embodiments herein can include two, three, or more energy bands. A line 402 shows the boundary between energy bands 1 and 2. Within each energy band, the X-ray energy spectrum can be approximated by one or more monochromatic energies. For the purpose of describing this invention, band 1 is approximated by three monochromatic energies 403, 404, and 405 and band 2 by monochromatic energies 406, 407, and 408. Reference energy levels for the respective bands, used in the processing procedure described subsequently, are shown at 409 and 411.

In general, the energy spectrum of each band i can be expressed as, $$I_i = \sum_{j=1}^{n} I_{ij} \quad (1)$$

where $I_{ij}$ is the intensity of the jth monochromatic energy in band i.

Figure 16:
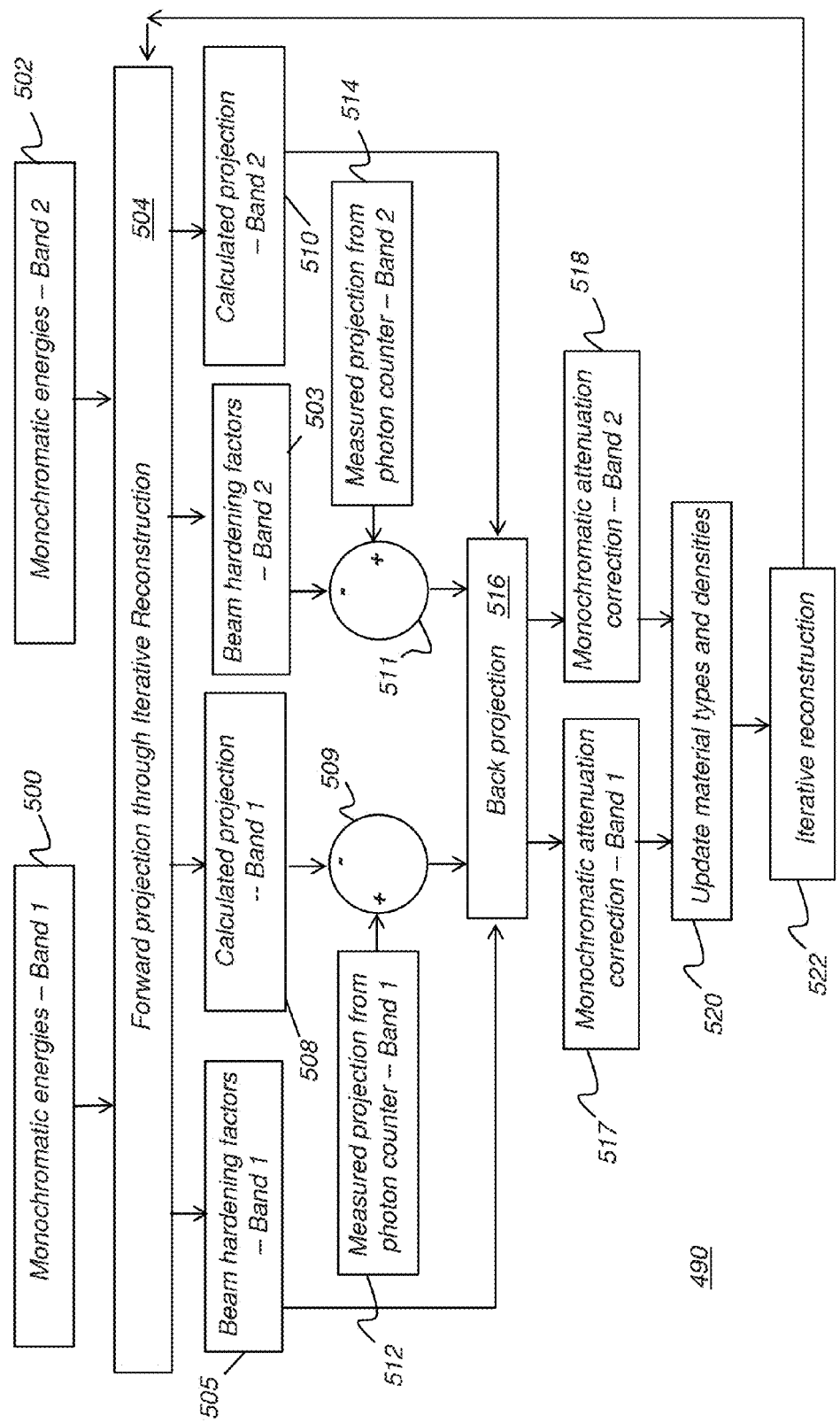
FIG. 16 is a logic flow diagram that shows a sequence for volume image reconstruction according to an embodiment of the present invention.

The logic flow diagram of FIG. 16 shows a multi-energy iterative reconstruction sequence 490 according to an embodiment of the present invention. The goal of these processing steps is to generate, from a standard volume reconstruction, a material or iterative reconstruction 522 of the scanned object. The iterative reconstruction 522 of the object is in terms of voxels that can be associated with one or more material types and associated density value(s). This reconstruction is typically initialized by performing a conventional filtered back-projection reconstruction, obtaining and using the measured projections 512 and 514 over a set of projection angles from bands 1 and 2, respectively. Alternate reconstruction methods can be used for initially forming the volume reconstruction that is needed at the outset of this process. Over successive processing iterations, as described subsequently, the initial volume reconstruction, with only a single effective attenuation value $\mu_{eff}$ for each voxel, is transformed into an iterative reconstruction that is provided by attenuation values at two or more reference energies. The polychromatic X-ray attenuation coefficients from these reconstructions 512 and 514 are used in place of the attenuation coefficient, at monochromatic reference energies, to estimate the iterative reconstruction 522 using an update step 520 as described following.

In a polychromatic forward projection step 504, the monochromatic energies 500 and 502 for band 1 and band 2, respectively, are used for forward projection through the initial reconstruction. In forward projection step 504, each individual ray, at each projection angle in the set of projection angles used for the measured projections, is traced from the X-ray source, through the object, and to each pixel of the detector, with analysis of attenuation values in small increments of size $\Delta t$. At a location x, y, and z that is inside the iterative reconstruction, the attenuation coefficient is determined at each monochromatic energy level in the band, using tri-linear interpolation of the attenuation coefficient of surrounding voxels. The calculation of the attenuation coefficient at a particular monochromatic energy for a voxel of the iterative reconstruction is specified by equation (8), which is described in more detail following. Model data values can be used in generating and processing the forward projection, including values that relate to attenuation data for different materials such as bone, adipose, soft tissue, fluid, and air. Model data values can be homogeneous, that is, at a single energy level. Typically, model values are derived from sampled results and calculations obtained to characterize attenuation characteristics for different materials.

The polychromatic attenuation coefficient for the band is calculated using the summed monochrome attenuation coefficients weighted by the intensity fraction at each monochromatic energy within band i, given by $I_{ij}$.

$$\mu_i^{poly} = \frac{\sum_{j=1}^{n} \mu_j I_{ij}}{I_i} \quad (2)$$

wherein $\mu_j$ is the X-ray attenuation coefficient at energy j. In addition to the polychromatic attenuation coefficient $\mu_i^{poly}$ a monochromatic attenuation coefficient $\mu_i^{ref}$ is calculated for the band at the selected monochromatic reference energy $E_i^{ref}$. This monochromatic reference energy is typically chosen to be within the band, but could alternately be outside of the band.

Continuing with the FIG. 16 sequence, an (x,y,z) position-dependent beam hardening factor 505, 503 for each band i inside the volume reconstruction is defined as:

$$H_i(x, y, z) = \frac{\mu_i^{ref}(x, y, z)}{\mu_i^{poly}(x, y, z)}. \quad (3)$$

After the beam hardening factor at a location is recorded and the polychromatic attenuation coefficient $\mu_i^{poly}$ is accumulated, the spectral distribution for each band is updated by:

$$I_{ij}^{p+1} = I_{ij}^p e^{-\mu_j \Delta t} \quad (4)$$

wherein $I_{ij}^p$ denotes the intensity of the jth monochromatic energy in band i at the pth increment in its travel along the ray extending from the source to the detector pixel. The result of step 504 is, for each band, a beam hardening factor 505, 503 at every voxel and a calculated forward projection 508 and 510. The value of a pixel of the calculated forward projection equals the sum of the $\mu_i^{poly}$ that are calculated as a ray is projected from the source to the detector pixel, multiplied by the ray increment $\Delta t$.

The calculated forward projections 508 and 510 are converted into photon counts by dividing the energy intensity at each detector pixel by the average energy of a photon for the band's energy spectrum at the detector pixel. In steps 509 and 511, a weighted error projection is calculated for each band. These steps include calculating the difference between the photon counts in the measured and calculated projections and weighting this difference using weights that depend on the geometry of the system. This difference is generally expressed in terms of the (-log) difference and is normalized by the incident photon intensity.

In a back projection step 516, the weighted error projection is back-projected to the reconstruction. In back-projection step 516 a ray is cast from the X-ray source through a voxel in the reconstruction and extended to a point on the detector. Bilinear interpolation of the weighted error projection is used to determine its value at the detector location. In steps 517, 518, this value is then translated to the attenuation correction value $\Delta \mu_i^{ref}$ at the reference monochromatic energy of band i by multiplication with the beam hardening factor $H_i(x,y,z)$ for the band at the location of the voxel.

In an update step 520, the iterative reconstruction is updated using the monochromatic attenuation correction values $\Delta \mu_i^{ref}$. The material composition at a voxel in this type of reconstruction can be represented in a variety of ways. One approach is to assume that each voxel is composed of several materials, each with a known mass density $\rho$ and X-ray mass attenuation coefficient $\mu^{mass}(E)$ which is known at all energies within the energy bands and the monochromatic reference energies. The attenuation coefficient at energy E is given by, $$\mu(E) = \sum_{i=1}^{n} w_i \rho_i \mu_i^{mass}(E) \tag{5}$$

where $w_i$ is the fraction of mass at the voxel that is of the ith material. Examples of materials that may constitute a voxel are water or other fluid, bone, adipose, blood, muscle, soft tissue, etc. Values for these materials can be obtained according to model data, for example. Classifier software may be used to obtain suitable values.

The choice of materials is based on prior knowledge of the scanned object. For the purpose of describing exemplary embodiments, the present description assumes a system with two energy bands and an imaged object formed of three materials. It is straightforward to generalize this approach to the case of more than two bands and fewer or more materials.

With two energy bands, the attenuation coefficients at the two monochromatic reference energies are related to the three-material composition at a voxel in the reconstruction by:

$$\mu_1^{ref} = w_1 \rho_1 \mu_1^{mass}(E_1^{ref}) + w_2 \rho_2 \mu_2^{mass}(E_1^{ref}) + (1-w_1-w_2) \rho_3 \mu_3^{mass}(E_1^{ref}) \tag{6}$$

$$\mu_2^{ref} = w_1 \rho_1 \mu_1^{mass}(E_2^{ref}) + w_2 \rho_2 \mu_2^{mass}(E_2^{ref}) + (1-w_1-w_2) \rho_3 \mu_3^{mass}(E_2^{ref}) \tag{7}$$

wherein $w_1$ and $w_2$ are the mass fraction of material 1 and 2, respectively, with the total mass normalized to unity (1.0). The set of two equations (6) and (7) can alternately be used to calculate $w_1$ and $w_2$ given $\mu_1^{ref}$ and $\mu_2^{ref}$. The calculation of the attenuation coefficient $\mu^j$ at a monochromatic energy $E_j$ in a band, which is performed in the forward projection step 504, employs an equation which is analogous to equations (6) and (7), $$\mu_j = w_1 \rho_1 \mu_1^{mass}(E_j) + w_2 \rho_2 \mu_2^{mass}(E_j) + (1-w_1-w_2) \rho_3 \mu_3^{mass}(E_j) \tag{8}$$

The iterative reconstruction 522 is represented by three materials and the mass fractional values of $w_1$ and $w_2$ for two of the materials at each voxel. In each iteration of the reconstruction method, the current reconstruction and equations (6) and (7) are used to calculate $\mu_1^{ref}$ and $\mu_2^{ref}$. The values of $\mu_1^{ref}$ and $\mu_2^{ref}$ are then updated by adding $\Delta \mu_1^{ref}$ and $\Delta \mu_2^{ref}$, respectively. The updated values of $\mu_1^{ref}$ and $\mu_2^{ref}$ are then used in update step 520 to re-determine the three materials at a voxel and their mass fractions $w_1$ and $w_2$.

In update step 520, a classifier is used as a means to determine the optimal choice of the three materials at a voxel from a list of possible materials, based on the current value of $\mu_1^{ref}$ and $\mu_2^{ref}$. Any of a number of types of classifier software known in the art can be used for providing instructions that accomplish this purpose, including neural networks, linear classifiers, support vector machines, k-nearest neighbor, Bayesian, and quadratic classifiers, for example. The material selection process is also based on the material content of surrounding voxels. Consistency with the material composition of neighboring voxels is incorporated into this step. This consistency may be based on the minimization of an energy function that is increased when nearby voxels or groups of voxels differ in composition. After material selection is complete, the inverse of equations (6) and (7) are used to calculate $w_1$ and $w_2$.

After the iterative reconstruction is updated, the next iteration begins with another forward-projection step 504. The iterative reconstruction method can be performed one projection at a time, so that after a single projection is processed, the reconstruction is updated. Alternatively, multiple projections or all of the projections can be processed before the 3D reconstruction is updated. The reconstruction method may be continued for a fixed number of iterations or until the iterative reconstruction process converges based on predetermined convergence criteria. An example of a convergence criterion is the relative amount of change from the previous iteration. This type of convergence criterion is met, for example, when the fraction of voxels that change material composition from the previous iteration to the present version is less than a specified value.

According to one embodiment, the material composition of a voxel can be estimated with some measure of accuracy using the iterative reconstruction values obtained from first and second energy bands. The material composition of one or more voxels can then be displayed to the viewer of the iterative reconstruction that is generated. According to an embodiment of the present invention, a mouse or other pointer is used to specify a voxel and display information about its probable material composition, as determined using the sequence of FIG. 16.

Embodiments of the present invention have been described with reference to an imaging system that utilizes a photon counting detector or other type of energy resolving detector that distinguishes at least first and second energy bands. However, alternate exemplary embodiments herein can also be used for radiographic imaging systems with any detector that directly or indirectly detects X-ray intensity. In general, exemplary methods can be applied where calculated projections 508 and 510 and measured projections 512 and 514 use a consistent metric of X-ray intensity.

Figure 17:
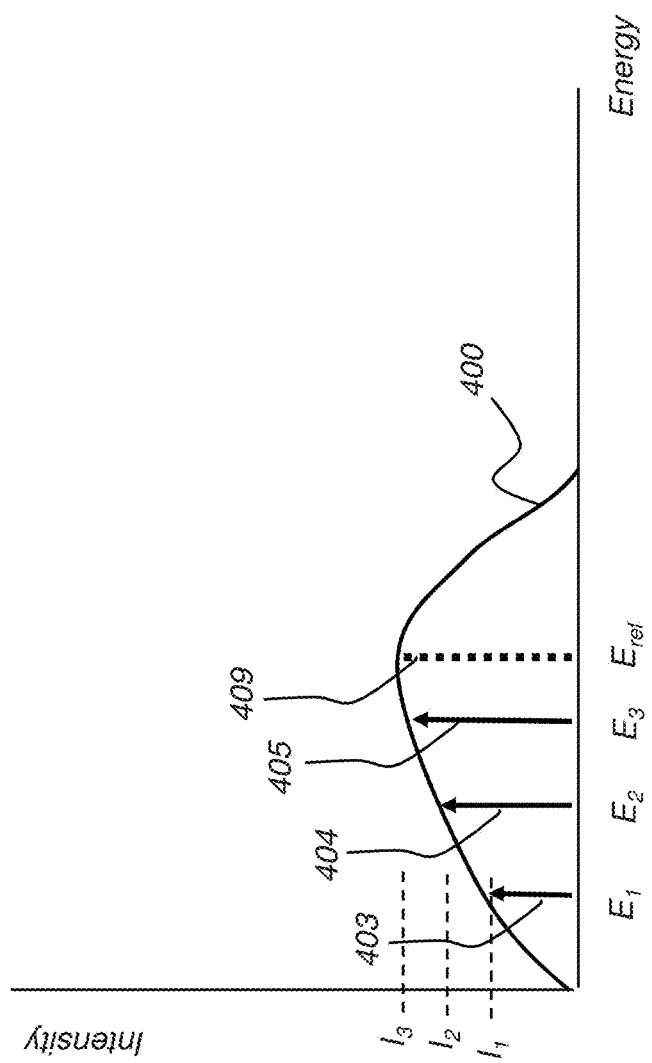
FIG. 17 is a graph that shows an energy distribution for x-ray radiation from a conventional, polychromatic x-ray source.

The graph of FIG. 17 shows an energy distribution 400 for x-ray radiation from a conventional, polychromatic x-ray source. For this embodiment, the filtered X-ray spectrum is approximated by three monochromatic energies 403, 404, and 405. Also, a reference monochromatic energy 409 is chosen, preferably but not necessarily within the range of energy distribution 400.

Figure 18:
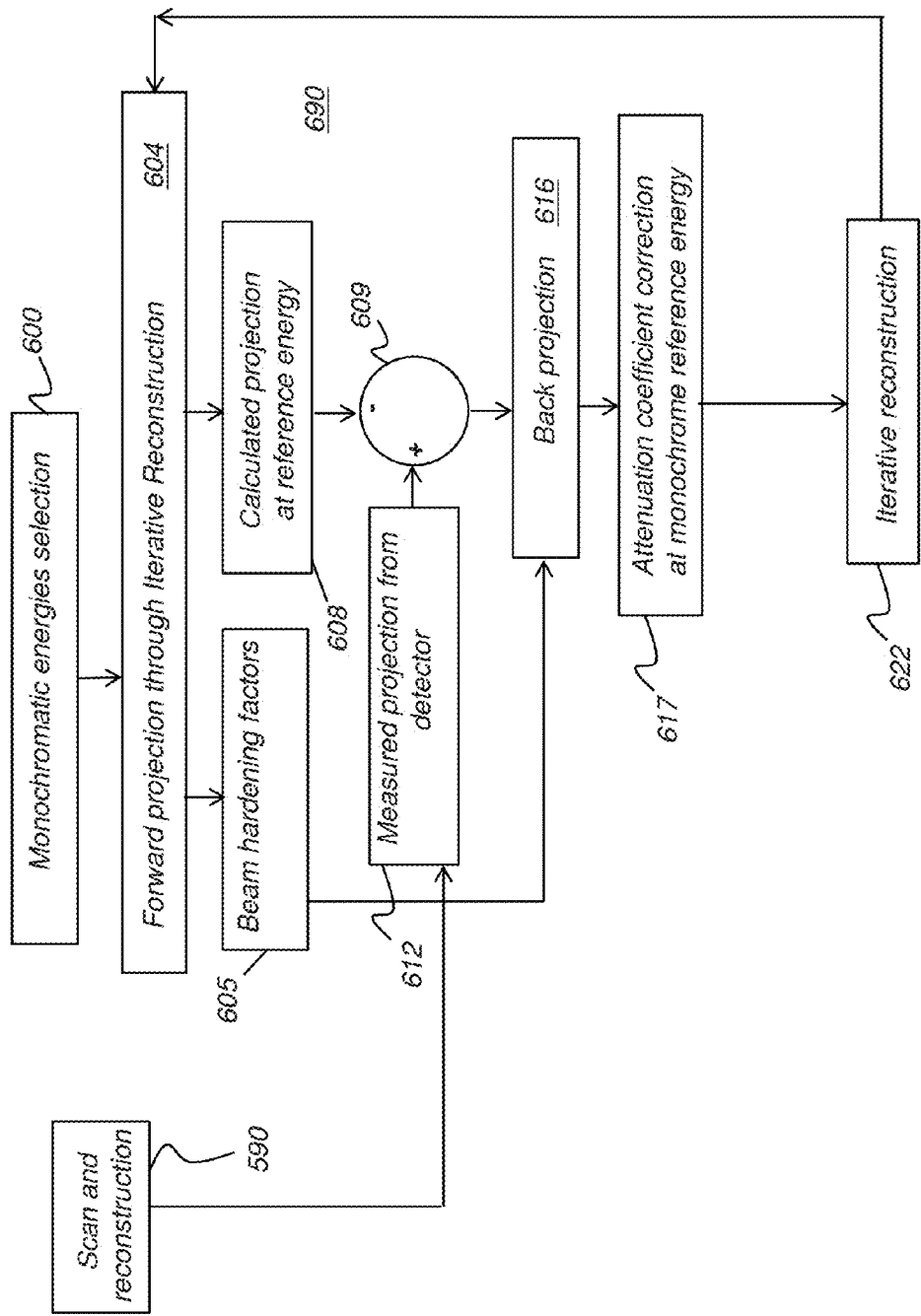
FIG. 18 is a logic flow diagram that shows an embodiment of a reconstruction sequence of the present invention that applies for a radiographic imaging system with a polychromatic x-ray source and a conventional x-ray detector.

The logic flow diagram of FIG. 18 shows an embodiment of a reconstruction sequence 690 of the present invention that applies for a radiographic imaging system with a polychromatic x-ray source and a conventional x-ray detector. The iterative reconstruction 622 of the object that is generated in this iterative sequence is in terms of voxels with one or more material types and associated density value(s) at the reference monochromatic energy 409. This information can be from model data, for example, or can be conditioned according to model data.

An initial scan and reconstruction processing step 590 is performed in order to obtain the projection data for the imaged object as a sequence of measured projections 612 that are used to support the iterative processing steps of reconstruction sequence 690. Initial reconstruction, such as using conventional FDK or other suitable filtered back-projection reconstruction algorithms, for example, is optional and can be helpful for defining the volume space for subsequent processing.

Reconstruction sequence 690 performs an iterative process that generates or predicts forward projection data, compares this data with actual measured projection data, and back-projects the error or difference data back to the volume image one or more times until the difference between the predicted and measured data is sufficiently small. Iterations can be performed one projection at a time, so that after image data from a projection is processed, the reconstruction can be updated; alternately, multiple projections, or all projections, can be processed before updating the 3D reconstruction. The reconstruction method may be continued for a fixed number of iterations or until the iterative reconstruction process converges based on predetermined convergence criteria. An example of a convergence criterion is the relative amount of change from the previous iteration.

Exemplary embodiments can use the fact that, for energy at a given wavelength, such as energy $E_1$ at 403 in FIG. 17, for example, the attenuation of that energy as provided in terms of signal intensity $I_1$ has the following relation:

$$\frac{\Delta I_1}{I_1} \propto e^{-\mu(E_1)\Delta d} \quad (9)$$

wherein $\Delta I_1$ is the change in intensity at the given wavelength or energy $E_1$ and $\Delta d$ is the depth or distance within the object imaged.

For the example of three selected monochromatic energies E1, E2, and E3 with corresponding intensities I1, I2, and I3, the polychromatic attenuation coefficient is given as:

$$\mu_{poly} = \frac{I_1\mu(E_1) + I_2\mu(E_2) + I_3\mu(E_3)}{I_1 + I_2 + I_3} \quad (10)$$

At the reference frequency, a monochromatic attenuation coefficient is given as:

$$\mu_{ref} = \mu(E_{ref}) \quad (11)$$

At a particular voxel location (x,y,z), the position-dependent beam-hardening factor H is given as:

$$H(x, y, z) = \frac{\mu(E_{ref})(x, y, z)}{\mu_{poly}(x, y, z)} \quad (12)$$

Referring again to the FIG. 18 sequence, in a monochromatic energies step 600, the set of discrete monochromatic energies, shown as 403, 404, and 405 in FIG. 17, and the reference energy 409 $E_{ref}$ are determined. In a polychromatic forward projection step 604, the location of a ray is moved from the X-ray source to each pixel of the detector in small increments of size $\Delta t$. At a location x, y, and z that is inside the reconstruction, surrounding voxels are identified. Voxel values are assumed at the attenuation coefficient for the reference monochromatic energy. Model data can be used for the forward projection processing.

The result of step 604 is a calculated projection 608 for a polychromatic source. In a step 609, this projection is subtracted from the measured projection 612 and weights that are determined by the geometry of the system and reconstruction are applied to create a weighted error projection. In a back projection step 616, the weighted error projection is back-projected to each voxel and the error is multiplied by the beam hardening factor H (eq. 12) at the voxel in order to calculate the attenuation coefficient correction at the monochromatic reference energy in a step 617. The attenuation coefficient corrections are used to update reconstruction 622. The voxels of this reconstruction tend to converge to the X-ray attenuation coefficients at the reference monochromatic energy as this process is repeated (iterated). Since, reconstruction 622 is in terms of attenuation coefficients for a monochromatic X-ray source, rather than for a polychromatic source, beam hardening artifacts can be greatly reduced.

The attenuation coefficient $\mu$ is used to determine the material composition of each voxel. This determination can be performed using one of a number of classifiers know in the art. After material classification, the interpolated polychromatic attenuation coefficient is determined based on the relative intensity of the monochromatic energies. Also, the beam hardening factor 605 at the location is calculated and the intensity of the monochromatic energies is updated.

A first example embodiment can provide a method for forming a three-dimensional reconstructed image of an object can include obtaining a plurality of two dimensional measured radiographic projection images scanned over a set of projection angles about the object; forming a volume reconstruction comprising image voxels having values representative of the scanned object by back projection of the measured projection image data; iteratively modifying the volume reconstruction voxel values to generate an iterative reconstruction by repeating, for a plurality of angles in the set of projection angles and for each of a plurality of pixels of the detector, by: generating a forward projection that includes calculating an x-ray spectral distribution at each volume reconstruction voxel, calculating an error value by comparing the generated forward projection value with the corresponding measured projection image value from the corresponding measured projection image, and adjusting one or more voxel values in back projection using the calculated error value and the x-ray spectral distribution at the voxel; and displaying the generated iterative reconstruction.

A second example embodiment can provide a method to form a three-dimensional reconstructed image of an object from a plurality of two-dimensional image projections that can include a) obtaining the plurality of two dimensional image projections as a sequence of measured image projection data taken over a range of angles, b) generating a forward projection of the object according to attenuation data obtained from a set of model data, c) calculating a beam hardening factor for each pixel according to the forward projection data, d) comparing the generated forward projection with the measured image projection data and generating a back projection according to the comparison and according to a plurality of beam hardening factors calculated according to the forward projection, e) adjusting the attenuation coefficients for the set of model data according to the generated back projection, f) repeating b) through e) one or more times to form the three-dimensional reconstructed image, and g) displaying, storing or transmitting the three-dimensional reconstructed image.

In one example embodiment, beam hardening factors can be computed as the ratio of monochromatic to polychromatic attenuation for a voxel of the reconstructed image. In one embodiment, the obtained image projections can be processing using filtered back projection. In one embodiment, f) is repeated a predetermined number of times. One embodiment can include calculating a difference between a back projection formed using the measured image projection data and the back projection generated according to the comparison. One embodiment can include displaying the material type for one or more voxels of the image of the three-dimensional reconstructed image. In one embodiment obtaining the plurality of two dimensional image projections can include obtaining the image projections on a photon-counting detector. The model data can be homogeneous, at a single energy level, and can include attenuation data taken from attenuation values for one or more of air, fluid, soft tissue, adipose, and bone, for example.

A third example embodiment can provide a method for forming a three-dimensional reconstructed image of an object that can include acquiring a plurality of two dimensional measured radiographic projection images scanned over a set of projection angles about the object, wherein the measured projection image data is obtained from an energy resolving detector that distinguishes at least first and second energy bands; forming a volume reconstruction comprising image voxels having values representative of the scanned object by back projection of the measured projection image data; iteratively modifying the volume reconstruction voxel values to generate an iterative reconstruction by repeating, for a plurality of angles in the set of projection angles and for each of a plurality of pixels of the detector, by: generating a forward projection that includes information from both the first and second energy bands, calculating an error value by comparing the generated forward projection value with the corresponding measured projection image value from the corresponding measured projection image, and adjusting one or more voxel values in back projection using the calculated error value; and displaying the generated iterative reconstruction.

The invention has been described in detail with particular reference to a exemplary embodiments, but it will be understood that variations and modifications can be effected within the spirit and scope of the invention. For example, sensor 121 can be a photon-counting sensor or an integrating image sensor. In addition, while a particular feature of the invention can have been disclosed with respect to at least one of several implementations/embodiments, such feature can be combined with one or more other features of the other implementations/embodiments as can be desired and advantageous for any given or particular function. The term "at least one of" is used to mean one or more of the listed items can be selected.

"Exemplary" indicates the description is used as an example, rather than implying that it is an ideal. The presently disclosed embodiments are therefore considered in all respects to be illustrative and not restrictive.

The invention claimed is:

1. A method for forming a three-dimensional reconstructed image of an object, the method comprising:
   a) acquiring a plurality of two dimensional measured radiographic projection images scanned over a set of projection angles about the object, wherein the measured projection image data is obtained from an energy resolving detector that distinguishes at least first and second energy bands from within an initial x-ray spectrum of an x-ray beam;
   b) forming a volume reconstruction comprising image voxels having values representative of the scanned object by back projection of the measured projection image data;
   c) iteratively modifying the volume reconstruction voxel values to generate an iterative reconstruction by repeating, for a plurality of angles in the set of projection angles and for each of a plurality of pixels of the detector, the steps of:
   generating a forward projection that includes calculating an x-ray spectral distribution at each volume reconstruction voxel,
   calculating an error value by comparing the generated forward projection value with the corresponding measured projection image value from the corresponding measured projection image, and
   adjusting one or more voxel values in back projection using the calculated error value and the x-ray spectral distribution at the voxel;
   and
   d) displaying the generated iterative reconstruction;
   wherein the energy resolving detector is a photon-counting detector, where the voxel values are adjusted according to a ratio of the attenuation coefficient at the spectral distribution at the voxel to the attenuation coefficient at a monochromatic x-ray energy.

2. The method of claim 1 further comprising adjusting the one or more voxel values to compensate beam hardening according to a ratio of a weighted average attenuation coefficient to a reference attenuation coefficient.

3. The method of claim 1 wherein generating the forward projection further comprises using model data values that relate to materials including bone, adipose, soft tissue, fluid, and air.

4. The method of claim 1 wherein generating the iterative reconstruction comprises using values obtained over both first and second energy bands.

5. The method of claim 3 wherein the model data values are for three or more materials.

6. The method of claim 3 wherein the model data values are determined according to instructions from classifier software.

7. The method of claim 1 further comprising displaying information about the one or more materials in the iterative reconstruction.

8. The method of claim 1 wherein forming the volume reconstruction comprises using a filtered back projection.

9. The method of claim 3 wherein the model data values are based on an estimate of materials composition.

10. The method of claim 1 wherein iteratively modifying the volume reconstruction voxel values repeats a fixed number of times.

11. The method of claim 2 further comprising compensating beam hardening according to a ratio of a weighted average attenuation coefficient to a reference attenuation coefficient at a second reference wavelength.

12. The method of claim 1 further comprising terminating the iteration of step c) according to an amount of change in voxel values between successive iterations.

13. The method of claim 1 wherein iteratively modifying the volume reconstruction voxel values comprises generating the forward projection for all pixels of the detector.

14. A method for forming a three-dimensional reconstructed image of an object, the method comprising:
   a) acquiring a plurality of two dimensional measured radiographic projection images scanned over a set of projection angles about the object, wherein the measured projection image data is obtained from a photon-counting detector that distinguishes at least first and second energy bands from within an initial x-ray spectrum of an x-ray beam;
   b) using data from each of the first and second energy bands, forming a corresponding volume reconstruction comprising image voxels having values representative of the scanned object by back projection of the measured projection image data;
   c) iteratively modifying the volume reconstruction voxel values to generate an iterative reconstruction by repeating, for each angle in the set of projection angles and for each of a plurality of pixels of the detector, the steps of:
      (i) generating a forward projection according to data from a model, wherein the forward projection includes calculating an x-ray spectral distribution at each volume reconstruction voxel,
      (ii) calculating an error value according to a comparison of the generated forward projection value with the corresponding measured projection image value from the corresponding measured projection image over the corresponding energy band; and
      (iii) adjusting one or more voxel values in back projection using the calculated error value and the x-ray spectral distribution at the voxel;
   and
   d) displaying the generated iterative reconstruction;
   wherein the voxel values are adjusted according to a ratio of the attenuation coefficient at the spectral distribution at the voxel to the attenuation coefficient at a monochromatic x-ray energy.

15. A method for forming a three-dimensional reconstructed image of an object, the method comprising:
   acquiring a plurality of two dimensional measured radiographic projection images scanned over a set of projection angles about the object, wherein the measured projection image data is obtained from an energy resolving detector that distinguishes at least first and second energy bands from within an initial x-ray spectrum of an x-ray beam;
   forming a volume reconstruction comprising image voxels having values representative of the scanned object by back projection of the measured projection image data;
   iteratively modifying the volume reconstruction voxel values to generate an iterative reconstruction by repeating, for a plurality of angles in the set of projection angles and for each of a plurality of pixels of the detector, by:
      generating a forward projection that includes information from both the first and second energy bands, calculating an error value by comparing the generated forward projection value with the corresponding measured projection image value from the corresponding measured projection image, and adjusting one or more voxel values in back projection using the calculated error value and the x-ray spectral distribution at the voxel, where the voxel values are adjusted according to a ratio of the attenuation coefficient at the spectral distribution at the voxel to the attenuation coefficient at a monochromatic x-ray energy; and
   displaying the generated iterative reconstruction;
   wherein the energy resolving detector is a photon-counting detector.

* * * * *